US008071111B2

(12) United States Patent
Smith

(10) Patent No.: US 8,071,111 B2
(45) Date of Patent: Dec. 6, 2011

(54) VIRULENCE OF STREPTOCOCCI

(75) Inventor: Hilda Elizabeth Smith, Lelystad (NL)

(73) Assignee: Stichting Dienst Landbouwkundig Onderzoek, Wageningen (NL)

(*) Notice: Subject to any disclaimer, the term of this patent is extended or adjusted under 35 U.S.C. 154(b) by 0 days.

(21) Appl. No.: 12/592,923

(22) Filed: Dec. 3, 2009

(65) Prior Publication Data

US 2010/0136057 A1    Jun. 3, 2010

Related U.S. Application Data

(63) Continuation of application No. 11/499,884, filed on Aug. 3, 2006, now Pat. No. 7,670,835, which is a continuation of application No. 10/435,654, filed on May 9, 2003, now Pat. No. 7,109,006, which is a continuation of application No. PCT/NL01/00805, filed on Nov. 6, 2001.

(30) Foreign Application Priority Data

Nov. 9, 2000    (EP) .................................... 00203947

(51) Int. Cl.
*A61K 39/09* (2006.01)
(52) U.S. Cl. ............... 424/244.1; 424/185.1; 424/190.1; 435/975
(58) Field of Classification Search .................. None
See application file for complete search history.

(56) References Cited

U.S. PATENT DOCUMENTS

| | | | |
|---|---|---|---|
| 5,610,011 A | 3/1997 | Smith et al. | |
| 5,681,570 A | 10/1997 | Yang et al. | |
| 5,733,765 A | 3/1998 | Mollet et al. | |
| 5,786,184 A | 7/1998 | Mollet et al. | |
| 5,928,900 A | 7/1999 | Masure et al. | |
| 5,948,900 A | 9/1999 | Yother et al. | |
| 5,981,229 A | 11/1999 | Masure et al. | |
| 6,699,703 B1* | 3/2004 | Doucette-Stamm et al. | 435/252.3 |
| 7,109,006 B2 | 9/2006 | Smith | |
| 7,125,548 B2 | 10/2006 | Smith | |
| 2002/0055168 A1 | 5/2002 | Smith | |
| 2007/0053938 A1 | 3/2007 | Smith | |

FOREIGN PATENT DOCUMENTS

| | | |
|---|---|---|
| EP | 0 750 043 B1 | 5/2001 |
| WO | WO 92/16630 | 10/1992 |
| WO | WO 95/06732 | 3/1995 |
| WO | WO 95/31548 | 11/1995 |
| WO | WO 96/21465 | 7/1996 |
| WO | WO 98/19689 A | 5/1998 |
| WO | 00/06738 A3 * | 2/2000 |
| WO | WO 00/05378 | 2/2000 |
| WO | WO 02/38597 A2 | 5/2002 |
| WO | WO 02/061070 A2 | 8/2002 |

OTHER PUBLICATIONS

Murphy et al. Pediatr. Infect. Dis. J. 1989. 8: S66-S68.*
Yamanaka et al (J. Pediatrics. 1993. 122(2): 212-218).*
Fraser et al (Science. 1998. 281: 375-388).*
Nelson et al (Nature. 1999. 399: 323-329).*
1997/1998 Stratagene catalog (p. 118, 1997/1998).
Allgaier et al., Relatedness of *Streptococcus suis* isolates of various serotypes and clinical backgrounds as evaluated by macrorestriction analysis and expression of potential virulence traits. Journal of Clinical Microbiology, 2001, pp. 445-453, vol. 39, No. 2.
Busque et al., Immunization of pigs against *Streptococcus suis* serotype 2 infection using a live avirulent strain, Can J Vet Res., Oct. 1997, pp. 275-279, vol. 61, No. 4.
Charland et al., *Streptococcus suis* serotype 2 mutants deficient in capsular expression, Microbiology, Feb. 1998, pp. 325-332, vol. 144, No. 2.
Chothia et al., The Embo Journal, 1986, pp. 823-826, vol. 5, No. 4.
Christie et al., Expression of fibronectin-binding protein FbpA modulates adhesion in *Streptococcus gordonii*, Microbiology, 2002, pp. 1615-1625, vol. 148.
Courtney et al., Cloning, Sequencing, and Expression of a Fibronectin/Fibrinogen-Binding Protein from Group A *Streptococci*, Infection and Immunity, Sep. 1994, pp. 3937-3946, vol. 62, No. 9.
Database EMBL 'Online' McNab, *S. gordonii* partial aldB gene, cshA gene & fbpA gene, Database accession No. X65164, XP002213089, 2002.
De Greeff et al., Contribution of Fibronectin-Binding Protein to Pathogenesis of *Streptococcus suis* Serotype 2, Infection and Immunity, Mar. 2002, pp. 1319-1325, vol. 70, No. 3.
De Greeff et al., Distribution of Environmentally Regulated Genes of *Streptococcus suis* Serotype 2 among *S. suis* Serotypes and Other Organisms, Journal of Clinical Microbiology, Sep. 2002, pp. 3261-3268, vol. 40, No. 9.
Dutch Text Annual Report ID-DLO *Streptococcus Suis*, 1996, with English translation of said report.
Elliott et al., Streptococcal infection in young pigs. V. An immunogenic polysaccharide from *Streptoccocus suis* type 2 with particular reference to vaccination against streptococcal meningitis in pigs, Oct. 1980, pp. 275-285, vol. 85, No. 2.
Kawabata et al., Molecular cloning, sequence and characterization of a novel streptococcal phosphoglycerate dehydrogenase gene, Oral Microbiology and Immunology, 2000, pp. 58-62, vol. 15.
Joh et al., Role of fibronectin-binding MSCRAMMs in bacterial adherence and entry into mammalian cells, Matrix Biology, 1999, pp. 211-223, vol. 18.
Kolkman et al., Diversity of capsular polysaccharide synthesis gene clusters in *Streptococcus pneumoniae*, J. Biochem., May 1998, pp. 937-945, vol. 123, No. 5.

(Continued)

*Primary Examiner* — Jennifer Graser
(74) *Attorney, Agent, or Firm* — TraskBritt

(57) ABSTRACT

The invention relates to the field of diagnosis of and vaccination against Streptococcal infections and to the detection of virulence markers of Streptococci. The invention discloses a method for modulating virulence of a *Streptococcus*, the method comprising modifying a genomic fragment of *Streptococcus* wherein the genomic fragment comprises at least a functional part of a fragment identifiable by hybridization in *Streptococcus suis* to a nucleic acid or fragment thereof as shown in FIG. 5.

16 Claims, 10 Drawing Sheets

OTHER PUBLICATIONS

Figure 1:
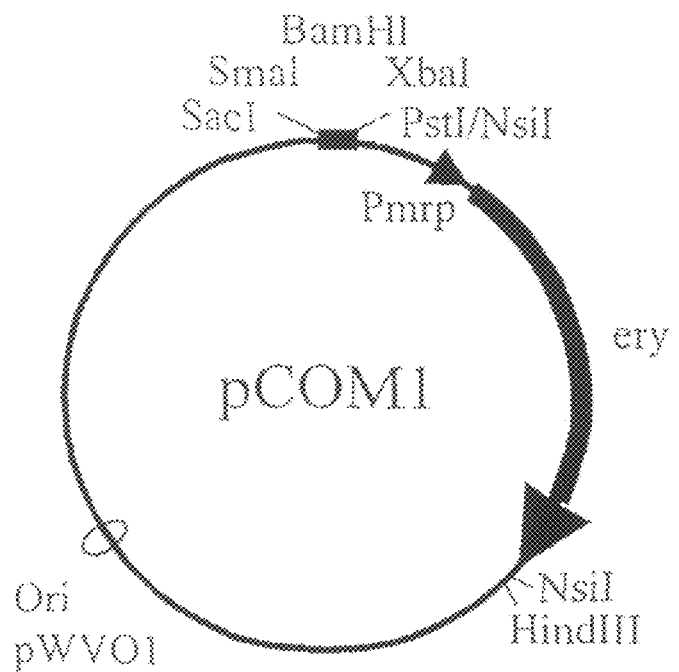

Koskiniemi et al., Identification of two genes, cpsX and cpxY, with putative regulatory function on capsule expression in group B streptococci, FEMS Immunology and Medical Microbiology, 1998, pp. 159-168, vol. 21.

McNab, Cloning and sequence analysis of thymidine kinase from the oral bacterium *Streptococcus gordonii*, FEMS Microbiology Letters, 1996, pp. 103-110, vol. 135.

Munoz et al., Characterization of IS1515, a Functional Insertion Sequence in *Streptococcus pneumoniae*, Journal of Bacteriology, Mar. 1998, pp. 1381-1388, vol. 180, No. 6.

PCT International Preliminary Examination Report, PCT/NL01/00805, dated Sep. 8, 2002, 2 pages.

PCT International Search Report, PCT/NL01/00805, dated Jun. 6, 2002, 3 pages.

Quessy et al., Immunization of mice against *Streptococcus suis* serotype 2 infections using a live avirulent strain, Can J. Vet Res., Oct. 1994, pp. 299-301, vol. 58, No. 4.

Roberts et al., The biochemistry and genetics of capsular polysaccharide production in bacteria, Ann. Rev. Microbiol., 1996, pp. 285-315, vol. 50.

Segers et al., Characterisation of the gene encoding suilysin from *Streptococcus suis* and expression in field strains, FEMS Microbiology Letters, 1998, pp. 255-261, vol. 167.

Smith et al., Cloning and nucleotide sequence of the gene encoding the 136-kilodalton surface protein (muramidase-released protein) of *Streptococcus suis* type 2, Infection and Immunity, 1992, pp. 2361-2367, vol. 60, No. 6.

Smith et al., Environmentally regulated genes of *Streptococcus suis*: identification by the use of iron-restricted conditions in vitro and by experimental infections of piglets, Microbiology, 2001. pp. 271-280, vol. 147.

Smith et al., High efficiency transformation and gene inactivation in *Streptococcus suis* type 2, Microbiology, Jan. 1995, pp. 181-188, vol. 141.

Smith et al., Identification and characterization of the cps locus of *Streptococcus suis* serotype 2: the capsule protects against phagocytosis and is an important virulence factor, Infect Immun., Apr. 1999, pp. 1750-1756, vol. 67, No. 4.

Smith et al., Mutants of *Streptococcus suis* Types 1 and 2 Impaired in Expression of Muramidase-Released Protein and Extracellular Protein Induce Disease in Newborn Germfree Pigs, Infection and Immunity, Oct. 1996, pp. 4409-4412, vol. 64, No. 10.

Smith et al., Repeats in an extracellular protein of weakly pathogenic strains of *Streptococcus suis* type 2 are absent in pathogenic strains, Infection and Immunity, 1993, pp. 3318-3326, vol. 61, No. 8.

Smith et al., Selection of virulence-associated determinants of *Streptococcus suis* serotype 2 by in vivo complementation, Infection and Immunity, Mar. 2001, pp. 1961-1966, vol. 69, No. 3.

Smith et al., The cps locus of *Streptococcus suis* serotype 2: genetic determinant for the synthesis of sialic acid, Microbial Pathogenesis, 2000, pp. 127-134, vol. 29, No. 2.

Watson et al., Pneumococcal Virulence Factors and Host Immune Responses to Them. European Journal of Clinical Microbiology & Infectious Diseases, Jun. 1995, pp. 479-490, vol. 14, No. 6.

Office Action for U.S. Appl. No. 10/632,117, dated Jun. 10, 2004.
Office Action for U.S. Appl. No. 10/632,117, dated Nov. 3, 2004.
Office Action for U.S. Appl. No. 10/632,117, dated Jul. 26, 2005.
Office Action for U.S. Appl. No. 10/632,117, dated Oct. 3, 2007.
Office Action for U.S. Appl. No. 10/632,117, dated Jun. 20, 2008.
Office Action for U.S. Appl. No. 10/632,117, dated Dec. 23, 2008.
Office Action for U.S. Appl. No. 10/632,117, dated Jun. 16, 2009.
Office Action for U.S. Appl. No. 11/516,691, dated Feb. 26, 2008.
Office Action for U.S. Appl. No. 11/516,691, dated Apr. 22, 2008.
Office Action for U.S. Appl. No. 11/516,691, dated Dec. 5, 2008.
Office Action for U.S. Appl. No. 11/516,691, dated Jun. 22, 2009.
Office Action for U.S. Appl. No. 11/516,691, dated Nov. 25, 2009.

Database EMBL [Online] *Streptococcus pneumoniae* adherence and virulence protein A (pavA) gene, complete cds, Nov. 4, 1999, XP002332859, retrieved from EBI accession No. EM_PRO:AF181976, Database accession No. AF181976.

Database EMBL [Online], *S.gordonii* partial aldB gene, cshA gene & fbpA gene, XP002332860 retrieved from EBI accession No. EM_PRO:SGSCHAG, Database accession No. X65164, 2002.

EMBL Nucleotide Sequence Entry EMBLCDS:AAL85276 (visited Feb. 18, 2009), <http://srs.ebi.ac.uk/srsbin/cgi-bin/wgetz?-e+[EMBLCDS:AAL85276]+-NEWiD>.

European Search Report, EP 02 71 1531 dated Jun. 22, 2005.

Greenspan et al., Nature Biotechnology, 1999, pp. 936-937, vol. 7.

Hampson et al., Journal of Clinical Microbiology, 1993, pp. 2895-2900, vol. 31, No. 11.

Herbert et al eds, The Dictionary of Immunology, Academic Press, 1995.

Holmes et al., The pavA gene of *Streptococcus pneumoniae* encodes a fibronectin-binding protein that is essential for virulence, Molecular Microbiology, 2001, pp. 1395-1408, vol. 41, No. 6.

Jadoun et al., Feb. 25, 2000, Mutation in crsR global regulator reduces *Streptococcus pyogenes* internalization, Microbial Pathogen., pp. 311-317, vol. 29.

Janeway-Travers, 1997, Immunobiology: The Immune System in Health and Disease, 3rd Edition.

Mikayama et al., Nov. 1993, Proc. Natl. Acad. Sci., USA., pp. 10056-10060. vol. 90.

Rudinger et al., Characteristics of the amino acids as components of a peptide hormone sequence, Peptide hormones, Biol. Council, Jun. 1976, pp. 1-7.

Sambrook et al., Molecular cloning: a laboratory manual, 2nd ed., 1989, Cold Spring Harbor Laboratory Press, Cold Spring Harbor, N.Y.

Smith et al., submitted Sep. 10, 2000, Genbank Accession No. AF306940.

Wisselink et al., Assessment of protective efficacy of live and killed vaccines based on a non-encapsulated mutant of *Streptococcus suis* serotype 2, Veterinary Microbiology, 2002, pp. 155-168, vol. 84.

Brazeau et al, (Microbiology, 142:1231-1237, 1996).

Devriese et al., Avian Pathology, 1994, pp. 721-724, vol. 23.

Ellis, R.W. (Chapter 29 of "Vaccines" Plotkin, S.A. et al. (eds) published by W. B. Saunders company (Philadelphia) in 1988, especially p. 571.

Gottschalk et al., Journal of Clinical Microbiology, Dec. 1999, pp. 4202, vol. 37, No. 12.

Merriam-Webster Online Dictionary, (visited Jun. 7, 2004) <http://www.m-w.com/cgi-bin/dictionary?book=Dictionary&va=vaccine&x=19&y=12>.

Reams et al., J. Vet. Diagn Invest, 1996, pp. 119-121, vol. 8.

Segura et al., FEMS Immunology and Medical Microbiology, 1998, pp. 189-195, vol. 12.

Staats et al., Veterinary Research Communications, 1997, pp. 381-407, vol. 21.

Baums et al., Clinical and Vaccine Immunology, Feb. 2009, pp. 200-208, vol. 16, No. 2.

Merck Manual On-line Streptococcal Disease (pp. 1-6), retrieved from web on Nov. 16, 2009.

Uniprot Q8RP86 (visited Dec. 3, 2009), <http://www.uniprot.org/uniref/?query=Q8RP86+AND+identity%3A0.5>.

UniProtKB/TrEMBL entry Q8RP86 (visited Dec. 3, 2009), <http://www.uniprot.org/Q8RP86>.

U.S. Appl. No. 11/499,884, filed Aug. 3, 2006, Hilda Elizabeth Smith, Virulence of *Streptococci*.

U.S. Appl. No. 11/516,691, filed Sep. 5, 2006, Hilda E. Smith, *Streptococcus suis* Vaccines and Diagnostic Tests.

U.S. Appl. No. 11/982,192, filed Oct. 31, 2007, Hilda E. Smith, Environmentally Regulated Genes of *Streptococcus suis*.

\* cited by examiner

```
                                                            ORF2 V10
                                                            ORF2 V735

1   MLPHNEADLCLHIMSPRVGILVLAESSAVNHCIRCRLHTAPFEKGAFEMEKKIPKLTV
                                                 MEKKIPKLTV

61   QLLAAIAMTLALMIVENYFSIRISDTLQVQFTFIPNTILGATAGPVWAAVFAAISDPVF
                                *  *  *                     *
      QLLAAIAMTLALMIAENHFSVRLSDTLQVQFTFIPNTILGATAGPVWAAVFAAISDPAF

121   VLFSGQIVLFIWILIEAVSAFTYGWFFYRKPLDTKNKADWLYVAGVVLLIQVVISFTMTP
                 **  *
      VLFSGQSMLFSFILIEAVSAFTYGWFFYRKPLDTKNKADWLYVAGVVLLIQVVISFTMTP

181   IALHFHFGTPWIVLYSSRLIKAVEEIPLRIVVTMLVLPSLQKIPELAKLMGIK  (SEQ ID NO:10)
      IALHFHFGTPWIVLYSSRLIKAVEEIPLRIVVTMLVLPSLQKIPELAKLMGIK  (SEQ ID NO:11)
```

FIG. 4A

|     |                                                                                                              |              |
| --- | ------------------------------------------------------------------------------------------------------------ | ------------ |
| 1   | MNYQETRRWLSSRPASDLENGVARVNWILERLDNPQLQVPTVHFVGINGKGSTLNALQSI                                                  | ORF3 V10     |
|     | MNYQETRRWLSSRPASDLENGVARVNWILERLDNPQLQVPTVHFVGINGKGSTLNALQSI                                                  | ORF3 V735    |
| 61  | LQSSDYTVGRFTSPSIIDFREQIVYQEMISEEDFARIVTDLQPLIEDLQTAGLDAISE                                                    |              |
|     | LRSSDYTVGRFTSPSIIDFREQIVFEQEMISEEDFARIVTDLQPLIEDLQTAGLDAISE                                                   |              |
|     |            *                                                                                                 |              |
| 121 | FEIVVVAMFVYFAHYQRPDILLVEAGMGGLQDATNVLAPLAVVCPSIGLDHQAFLGFTHA                                                  |              |
|     | FEIVVVAMFVYFAHYQRPDILLVEAGMGGLQDATNVLAPLAVVCPSIGLDHQAFLGFTHA                                                  |              |
| 181 | ALARHKVAVLREGVPLIYATDQPEVETVFEEHACQLQSPTYAVGREILLENSRAGFAVSS                                                  |              |
|     | ALARHKVAVLRERVPLLYATDQSEVVAAFEDHASQLQSPTYAVGREILLENSRAGFAVSS                                                  |              |
|     |      *    ***  *  *   **                                                                                     |              |
| 241 | PLGRVEELTIQMQGRHQEVNAALAVTTAQLIKPHFPTTTNETIRQGLSQAIWPGRLELIR                                                  |              |
|     | TLGRVEELTIQMQGRHQEVNAALAVTTAQLISPDEPTTTNETIRQGLSQAIWPGRLELIR                                                  |              |
|     | *                            *** *                                                                           |              |
| 301 | PNIMIDGAHNNESIAVLIQLLEEKYADRDIELLFAAINTKPVDQMLSQLSQFGPVSVTFE                                                  |              |
|     | PNIMIDGAHNNESIAVLIQLLEEKYADRDIELLFAAINTKPVDQMLSQLSQFGPVSVTFE                                                  |              |
| 361 | DDFRAVQLEDYPSGYERVQTYQEMVEQADLNPKKLYLITGSLYFTTVRKYILEEIV (SEQ ID NO:12)                                       |              |
|     | DDFRAVQLGDYPSGYERVQTYQEMLEQVDLLNPKQLYLITGSLYFTTVRKYILEEIV (SEQ ID NO:13)                                      |              |
|     |        *                 *   *   *                                                                           |              |

FIG. 4B

```
GGATCCTGCTATCATTCCTTATTTGATTGCGAATGTGAAGAACTGAAAGATGCTGCAGACGTTGTTAACATGTGAATA
AACAGTCAGGCTTATTCGGTGTGTATCTGGCTTCTCAAGTGATATGCGGTGATATTGAAGCAGGTATCCAAGCTCACAATCCA
GATGCAGTGTTGGCCTACAATATTTCATTGACCGTATTAAGAAATTTATCGCAGTTTTAAATGGGGC
AGATGCTATTGTCTTCACCGCTGGTATGGGTGAAAATGCACCGCTTATGCCAACTATGGTGACATTTCAACGCAGAATCAAAAGTTCGTGT
TTGGTATTGAGTTGGACCTACAAAAAAATGTATTCGGCAACTATGGTGACATTTCAACGCAGAATCAAAAGTTCGTGTC
TTGGTTATTCCGACGGATGAAGAATTGGTTATTGCGCGTGAAGTGGAACGCTTGAAATAAGAAAAACTAACTGGTAGTCG
GAGACTGCCAGTTCTCTTATAGTTTATACCTTAGAAAAGGTATAGTTTTAGCAAGTGACAAAATATATAGTGTGA
TACAATAGACTAGCAAAGAAATTTGCACAGAGTAGATGGTTTGCGTCAAGTGTATGTGGATGGTGTTGCCACATAACG
AAGCTGATCTTTGCTTGCATCTGATGTCTCCTAGAGTAGGAACATTGGTCCTGGCTGAGAGTAGCCGGTAAACCATTGC
ATCCGCTGCGAATACACACGACAGCTCCATTTTTTGAAAAGGAGCATTTTTATGGAAAAGAAAATCCAAAACTAAC
GGTGCAGTTGTTGGCTGCTATTGCGATGACCCTTGCCTTGGTCATGATTGTAGAGAACTATTCTCTATTCGGATTCTG
ATACTTTACAGGTTCAGTTTACCTTCATTCCAATACTATTTTGGGAGCTATTGCGGGTCCAGTTTGGGCAGCTGTCTTT
GCCGCTATTTCAGACCCAGTCTTTGTCTTCTTTGTTAGCGGGCAAACCGCTAGACACCAAGGTGCTCACTTGGATTTGATTGAGGCGGTATC
GGCATTTATCTACGGCTGGTTCTTCTATCGAAAACCGCTAGACACCGATGCCCTCCATTTGGCTCTATGTGGCTGGTG
TAGTTGTCTTGATTCAGGTTGGTTGCCTTGATTTCCTTTATCATGACAACAAGGCTGATTGGCTCATTTGAACACCTTGGATT
GTTCTGTATAGCAGTGCCTTGATTAAGGCAGTTTTGAAATTCCATTACGCATTGTCGTGACACATGCTGTCTTGCCAAG
TTTACAAAAAATACCTGAAATTGGCCAAGTTAATTATCAAGAAACTCGCCGGTGCATTAAATAAACAGTATCAAGCAACAGGTCATCCCCGTGTTGC
TACTTTTGTAGAGAGGAATCATGAATTGGATTTAGAAACGCTTAACTGGATTTTAGAAACGCTTCAAGTGGCTATCTAGTGTCCTGCATCAGATTTAGAAAA
TGGCGTTGCACGTGTCAACTGGATTTAGAAACGCTTACAGTCTATCTTCGGATTACACCGTCGGCCGCTTTACATCA
CAAATGGCAAGGGCTGACCCTCAACGCTTACAGTCTATCTTCGGATTACACCGTCGGCCGCTTTACATCA
CCGTCTATCATCATTGATTTTCGAGAGCAGATTTGGACCAGACGGCTGGACTGGATGCCATCTCGGAGTTTGAGATTGTAGTAGTGG
AGACTTGCAACCCTTGTCTACTTTGCCCACTACCAGCGTCCCGATATTCTCTTGGTGATGCCATCTCGGAGTTTGAGATTGTAGTAGTGG
CTATGTTTGTCTACTTTGCCCACTACCAGCGTCCCGATATTCTCTTGGTGAGGCCGGCATGGTGGTTTGCAGGATGCG
ACCAATGTCTTGCCCCCTTGGCAGTAGTTTGTCGTCCATCGGTTTGGACCATCAGGCATTTTGGGAGAGACCACGC
TGCTATAGCCGTCACAAGGTCGCCCTCTGCCTCTGAGGGGTTCCGCTCATCTATGGACCGACCAGCAGAAGTGAGA
CAGTATTGAGGAGCATGCCTGTCAGCTTCAGATGCCGAGTCCGACCTATGCGGTGGGGGAGATTCTTTTGAAATAGCAGA
GCAGGCTTTGCAGTTTCAAGTCCTCTCGGCCGTGTGAAGAGTAACACTACAGATGCAGGTCGTCACCAGGAGGTCAA
TGCAGCCTTGGCAGTGACAACAGCTCAGCTCATTAAACCTCATTTCCAACAATTACCAATGAAACCATCCGGCCAGGGCT
```

FIG. 5A - V10 seq.

TGTCCAAGCCATCTGGCCGGGTCGCTTAGAGTTGATTAGGCCTAATCTCATGATTGACGGTGCCACAATAATGAAAGT
ATCGCCGTCCTGACACAACTCTTGGAAGAAAAGTATGCTGACAGGGATATTGAAATCCTCTTTGCGGCCATCAATACCAA
GCCAGTGGACCAGATGTTGTCCCAGCTTAGCCAATTTGGACCTGTTAGCGTGACGATTTCAGAGCGGTAC
AGTTAGAAGATTATCCGTCAGGCTATGAACGAGTTCAGACCTATCAGGAGTGGGTGGAGCAGGCGGACTTGGACAATCCC
AAAAACTCTACCTGATTACAGACGCTCGCTATATTTCATTACCTATGTGAGGAAGTACATTTTAGAAGAACTGTTTAGAA
AAAAAGGCTTTGCCGGGCATTCAACCAGCAAAGTCTTTTGTTTTAATAATTTTAATCAAATCAACCGTTGAGCGGTC
TAGTTTTTTAACGATGGTCTGCAAGAAGGCTTGGCCTCTAAGAAGTCATCCATGCTGTAGAGAGTTTGATGTGAATGGA
TGTAGCGAGCGCAGACACCGATAGTTGTTGATGGAACACCATGATTTTCAAGTGGGCTGCACCAGCATCTGTTCCACCT
TTACCACAGTAGTATTGGAATTTGACACCTGCTTCTCGGCAGTTGTGAGGAGGAAGTCTTTCATGTTTTTAACATGAT
GTGACCTGGATCC (SEQ ID NO:14)

FIG. 5A V10 seq. cont'd.

```
CTGCAGATGTTGTGAAACATGTTGAATAAACAGTGAGGCTTGTTCGGTGTATCTGGCTTCTCAAGTGATATGCGTATATT
GAAGCAGGCATCCAAGCTCACAATCCAGATGCAGTGTTGGCCTACAATATTTCATTGACCGTATTAAGAAATTTATCCG
TCAGTATCTTGCAGTTTTAAATGGGCAGAATGCTATTGTCTTCACGGCTGGTATGGGTGAAAATGCACCGCTTATGCGCA
ATGACGTAGTAGAAGGCTTGTCTTGGTTGTGAGTTGGACCCACAAAAAAATGTATTTGGCAACTATGTGACATT
TCAACGGCAGAATCAAGGGTTCGTCTCTTGGTTATTCCGACGGATGAAGAATTGGTTATTGCGCGTGAAGTGAACGTTT
GAAATAAGACAAAACTAACTGGTAGTCGGAGACTGCGCGGTTCTCTTATAGTTTATACCTTTAGAAAGGTATAGTTTTTAG
CAAGTGGTCAAAATATATGTGTGATACAATAGACAAGCTCAATCTTTGCTTGCATCTGATGTCTCCTAGAGTAGGAACATGTCTCAAGTGT
ATGTGGATGGGATGTTGCCACATAAACGAAGCTGATCTTTGCTTGCATCTGATGTCTCCTAGAGTAGGAACATTGGATCTG
GCTGAGAGTAGCGCGGTAAACCATTGCATCCGCTGTGAATACACGACCAGCTCCATTTTTGAAAAGGAGCATTTTT
ATGGAAAAGAAGATTCCAAAACTAACGGTGCAGTTGTGCTGCTATGGCAGTGATGACTCTGCCTGGTCATGATTGCGGA
GAACCATTTCTGTTCGTCTTTCGATACCTTGCAGTCCAGTTACCTTTACCTTATCCTAATACTATTTAGGTGCGATG
CTGGTCCTGTTTGGGCTGCTGATTGCGGCGATTCAGACCCAGCTTTGTCTTGTTAGTGACAGAGCATGCTTTT
AGTTTATCTTGATTGAGCGGTATCGGCTTTTATCTATGCTGGTTCTGATTCAGGTTGTGATTTCCTTATCATGACACCGATTGCCCTCC
GGCTGATTGGCTCTATGTTGCAGGGGTTGTTGTCTTGATATAGCAGTCAGTTCAGGTTGTGATTTCCTTATCATGACACCGATTGCCCTCC
ATTTCCATTTTGGAACACCTTGGATTGTTCGTCTTGCTCTGTATAGCAGTCAGTTCAGGTTGTGATTTCCTTATCATGACACCGATTGCCCTCC
GTCGTGACTATGCTTGTCTTACCAAGTTGCTCCTTTGTAGAGAGGAATCATGATTTGCACGTGTCAACTGGATTTAATGGCATTAAATAAACAGTAT
CAAGCAACAGGTCATCCCCCTGTTGCTCCTTTGTAGAGAGGAATCATGATTTGCACGTGTCAACTGGATTTGGAACACCTTGGACAATCCCCAGCTTCA
AGTCGTCCTGCATCAGATTTAGAAAATGGCGTTGCACGGCTAGTGCAAGGGCTCAACGGCTTACAGTCTATCTTACGGTCTTCGG
AGTGCCGACCGTTCACTTCGTAGTACAAATGGCACAAATGGCTACAGCTTCAACCGCCTGACCCTCCAACGCCTTACAGTCTATCTTACGGTCTTCGG
ATTACACCGTCGGTCGTTACCTCACCGTCATCATTGATTCAACCTTGATCATTGATTTCGACCTGAGACTGGACCAGACGCTGACTGGATGCCAT
GAGGAAGATTTGCAAGGATTGTGACAGATTGTGATGGCTATGTTGTCTACTTTGCCCATTGCACCGTCCGACATTCTCTTGGTGAGG
CTCGGAGTTTGAGATTGTAGTAGTGGCTATGTTGTCTACTTTGCCCATTGCACCGTCCGACATTCTCTTGGTGAGG
CGGGACATGGTGGTTTGCAGGATGGGACCAATGTCTCTTGCCCATTGCACAAGGTTGCTGTCTTGCGTGGAGCGGGTTCCCTCCTCTA
CAGGCTTTTTGGGAGAGACCAGAAGTGGTGCAGCATTTGAGGATCACGCCAGTCAGCTTCAGAGTCCGACCTATGCGGTGGGAC
TGCCGACCGACCAGTCAGAAGTGGTGCAGCATTTGAGGATCACGCCAGTCAGCTTCAGAGTCCGACCTATGCGGTGGGAC
GGGAGATTCTTTTTGAAAATAGACAGAGGCTTGTGTTTCAAGTACTCTCGGCCGTGTGGAAGAATTAACACTGCAG
ATGCAGGGTCGTCACCAGGAGGTCAATGCAGCCTTGGCAGTGACAACAGCTCAGCCTGCTTCTCAGCCTGATTTTCAACAAT
TACCAATGAAACCATCCGCCAGGCTTGTCCCAAGCCATCTGGCCGGGCCATCTGGCCGGGCCATCCGCCCTAGAGTTGATTGATTAGGCCTAATCTCATGA
```

FIG. 5B V735 seq.

TTGACGGTGCCCACAATAATGAAAGTATCGCCGTCCTGACACAACTCTTGGAAGAAAAGTATGCTGACAGGGATATTGAA
ATCCTCTTTGCGGCCATCAATACCAAGCCAGTGACCAGTGACCAGATGTTGTCCCAGCTTAGCCAATTTGACCTGTTAGCGTGAC
GACCTTTGACGATTTCAGAGCGGTACAGTTAGGAGATTATCCGTCAGGCTATGAACGAGTTCAGACTTCAGGAGTGGT
TGGAGCAGGTGGACTTGGACAATCCCAAACAACTCTACTGATTACAGGCTCGCTATATTTCATTACCTATGTGAGAAG
TACATTTTAGAAGAACTGTATAGAAAAAAGGCTTTGCCGGGCATTCAACCCAGCAAAGTCTTTTGTTTTAATAATTTT
AATCAAATCAACCGTTGAGGCGGTCTAGTTTTTTAACGATGGTCTGCAAGAAGGCTTGGGCCTCTAAGAAGTCATCCATGC
TGTAGAGAGTTTGATGTGAATGGATGTAGCGAGCGCAGACACCGATAGTTGTTGATGGAACACCATGGTTTTCAAGTGG
GCTGCACCGGCATCTGTTCCACCTTTACCACAGTAGTATTGAATTTGACACCTGCTTCTCGGCAGTTGTGAGGAGGAA
GTCTTTCATGTTTTTAGCATGATGTGGCCTGGGTCATAGAAACGAAGCAGAGTTCCGTCACCAATTTTCCTTGGTCGC
CATAAATATCACCTGCGGGCGAGCAATCAACAGCGAGGAAAAATGTCTGATTGAACTTGGTTGTAGAGGCATGAGCACCA
CGAAGACCAACCTCTACTTGCACATTGGCCCAGCAATCAACTGATTTGCAAAGCTT (SEQ ID NO:15)

FIG. 5B V735 seq. cont'd.

MLPHNEADLCLHLMSPRVGTLVLAESSAVNHCIRCRIHTTAPFFEKGAFFMEKKIPKLTVQLLAAIAMTLALVMIVENYF
SIRISDTLQVQFTFIPNTILGAIAGPVWAAVFAAISDPVFVLFSGQTVLFTWILIEAVSAFIYGWFFYRKPLDTKNKADW
LYVAGVVVLIQVVISFIMTPIALHFHFGTPWIVLYSSRLIKAVFEIPLRIVVTMLVLPSLQKIPELAKLMGIK (SEQ ID NO:10)

FIG. 5C ORF 2 V10

MEKKIPKLTVQLLAAIAMTLALVMIAENHFSVRLSDTLQVQFTFIPNTILGAIAGPVWAAVFAAISDPAFVLFSGQSMLF
SFILIEAVSAFIYGWFFYRKPLDTKNKADWLYVAGVVVLIQVVISFIMTPIALHFHFGTPWIVLYSSRLIKAVFEIPLRI
VVTMLVLPSLQKIPELAKLMGIK (SEQ ID NO:11)

FIG. 5D ORF 2 V735

MNYQETRRWLSSRPASDLENGVARVNWILERLDNPQLQVPTVHFVGTNGKGSTLNALQSILQSSDYTVGRFTSPSIIDFR
EQIVYQQEMISEEDFARIVTDLQPLIEDLDQTAGLDAISEFEIVVVAMFVYFAHYQRPDILLVEAGMGGLQDATNVLAPL
AVVCPSIGLDHQAFLGETHAAIARHKVAVLREGVPLIYATDQPEVETVFEEHACQLQSPTYAVGREILLENSRAGFAVSS
PLGRVEELTLQMQGRHQEVNAALAVTTAQLIKPHFPTITNETIRQGLSQAIWPGRLELIRPNLMIDGAHNNESIAVLTQL
LEEKYADRDIEILFAAINTKPVDQMLSQLSQFGPVSVTTFDDFRAVQLEDYPSGYERVQTYQEWVEQADLDNPKKLYLIT
GSLYFITYVRKYILEELV (SEQ ID NO:12)

FIG. 5E ORF 3 V10

MNYQETRRWLSSRPASDLENGVARVNWILERLDNPQLQVPTVHFVGTNGKGSTLNALQSILRSSDYTVGRFTSPSIIDFR
EQIVFEQEMISEEDFARIVTDLQPLIEDLDQTAGLDAISEFEIVVVAMFVYFAHYQRPDILLVEAGMGGLQDATNVLAPL
AVVCPSIGLDHQAFLGETHAAIARHKVAVLRERVPLLYATDQSEVVAAFEDHASQLQSPTYAVGREILLENSRAGFAVSS
TLGRVEELTLQMQGRHQEVNAALAVTTAQLLSPDFPTITNETIRQGLSQAIWPGRLELIRPNLMIDGAHNNESIAVLTQL
LEEKYADRDIEILFAAINTKPVDQMLSQLSQFGPVSVTTFDDFRAVQLGDYPSGYERVQTYQEWLEQVDLDNPKQLYLIT
GSLYFITYVRKYILEELV (SEQ ID NO:13)

FIG. 5F ORF 3 V735

SEQUENCE LISTING

<160> NUMBER OF SEQ ID NOS: 15

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(30)

<400> SEQUENCE: 1
cgagctcgga agaattggtt attgcgcgtg                                    30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(29)

<400> SEQUENCE: 2
cgggatcccg ggggatgacc tgttgcttg                                     29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(31)

<400> SEQUENCE: 3
tcccccgggg gacaagcaac gggtcatccc c                                  31

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(30)

<400> SEQUENCE: 4
cgggatcccg gttgaatgcc cggcaaagcg                                    30

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: primer
<220> FEATURE:
<221> NAME/KEY: misc_feature
<222> LOCATION: (1)..(33)

<400> SEQUENCE: 5
tcccccgggg gagtcgtgtg tattcgacag cgg                                33

```
<210> SEQ ID NO 6
<211> LENGTH: 6
<212> TYPE: DNA
<213> ORGANISM: Artificial Sequence
<220> FEATURE:
<223> OTHER INFORMATION: Description of Artificial Sequence: Putative
      promoter sequence
<220> FEATURE:
<221> NAME/KEY: misc_feature
<222> LOCATION: (1)..(6)

<400> SEQUENCE: 6 tggaca                                                                 6

<210> SEQ ID NO 7
<211> LENGTH: 6
<212> TYPE: DNA
<213> ORGANISM: Artificial Sequence
<220> FEATURE:
<223> OTHER INFORMATION: Description of Artificial Sequence: Putative
      promoter sequence
<220> FEATURE:
<221> NAME/KEY: misc_feature
<222> LOCATION: (1)..(6)

<400> SEQUENCE: 7 tacaat                                                                 6

<210> SEQ ID NO 8
<211> LENGTH: 7
<212> TYPE: DNA
<213> ORGANISM: Artificial Sequence
<220> FEATURE:
<223> OTHER INFORMATION: Description of Artificial Sequence: Putative
      promoter sequence
<220> FEATURE:
<221> NAME/KEY: misc_feature
<222> LOCATION: (1)..(7)

<400> SEQUENCE: 8 atggaca                                                                7

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Putative
      promoter sequence
<220> FEATURE:
<221> NAME/KEY: misc_feature
<222> LOCATION: (1)..(6)

<400> SEQUENCE: 9 tggtca                                                                 6

<210> SEQ ID NO 10
<211> LENGTH: 233
<212> TYPE: PRT
<213> ORGANISM: Streptococcus suis
<220> FEATURE:
<221> NAME/KEY: SITE
<222> LOCATION: (1)..(233)
<223> OTHER INFORMATION: /note="ORF2 V10"

<400> SEQUENCE: 10

Met Leu Pro His Asn Glu Ala Asp Leu Cys Leu His Leu Met Ser Pro
 1               5                  10                  15

Arg Val Gly Thr Leu Val Leu Ala Glu Ser Ser Ala Val Asn His Cys
            20                  25                  30
```

```
Ile Arg Cys Arg Ile His Thr Thr Ala Pro Phe Phe Glu Lys Gly Ala
            35                  40                  45

Phe Phe Met Glu Lys Lys Ile Pro Lys Leu Thr Val Gln Leu Leu Ala
 50                  55                  60

Ala Ile Ala Met Thr Leu Ala Leu Val Met Ile Val Glu Asn Tyr Phe
 65                  70                  75                  80

Ser Ile Arg Ile Ser Asp Thr Leu Gln Val Gln Phe Thr Phe Ile Pro
                 85                  90                  95

Asn Thr Ile Leu Gly Ala Ile Ala Gly Pro Val Trp Ala Ala Val Phe
             100                 105                 110

Ala Ala Ile Ser Asp Pro Val Phe Val Leu Phe Ser Gly Gln Thr Val
         115                 120                 125

Leu Phe Thr Trp Ile Leu Ile Glu Ala Val Ser Ala Phe Ile Tyr Gly
     130                 135                 140

Trp Phe Phe Tyr Arg Lys Pro Leu Asp Thr Lys Asn Lys Ala Asp Trp
145                 150                 155                 160

Leu Tyr Val Ala Gly Val Val Leu Ile Gln Val Ile Ser Phe
                    165                 170                 175

Ile Met Thr Pro Ile Ala Leu His Phe His Phe Gly Thr Pro Trp Ile
                180                 185                 190

Val Leu Tyr Ser Ser Arg Leu Ile Lys Ala Val Phe Glu Ile Pro Leu
            195                 200                 205

Arg Ile Val Val Thr Met Leu Val Leu Pro Ser Leu Gln Lys Ile Pro
210                 215                 220

Glu Leu Ala Lys Leu Met Gly Ile Lys
225                 230
```

<210> SEQ ID NO 11
<211> LENGTH: 183
<212> TYPE: PRT
<213> ORGANISM: Streptococcus suis
<220> FEATURE:
<221> NAME/KEY: SITE
<222> LOCATION: (1)..(183)
<223> OTHER INFORMATION: /note="ORF2 V735"

<400> SEQUENCE: 11

```
Met Glu Lys Lys Ile Pro Lys Leu Thr Val Gln Leu Leu Ala Ala Ile
 1               5                  10                  15

Ala Met Thr Leu Ala Leu Val Met Ile Ala Glu Asn His Phe Ser Val
             20                  25                  30

Arg Leu Ser Asp Thr Leu Gln Val Gln Phe Thr Phe Ile Pro Asn Thr
         35                  40                  45

Ile Leu Gly Ala Ile Ala Gly Pro Val Trp Ala Ala Val Phe Ala Ala
 50                  55                  60

Ile Ser Asp Pro Ala Phe Val Leu Phe Ser Gly Gln Ser Met Leu Phe
 65                  70                  75                  80

Ser Phe Ile Leu Ile Glu Ala Val Ser Ala Phe Ile Tyr Gly Trp Phe
                 85                  90                  95

Phe Tyr Arg Lys Pro Leu Asp Thr Lys Asn Lys Ala Asp Trp Leu Tyr
             100                 105                 110

Val Ala Gly Val Val Leu Ile Gln Val Val Ile Ser Phe Ile Met
         115                 120                 125

Thr Pro Ile Ala Leu His Phe His Phe Gly Thr Pro Trp Ile Val Leu
     130                 135                 140

Tyr Ser Ser Arg Leu Ile Lys Ala Val Phe Glu Ile Pro Leu Arg Ile
```

```
            145                 150                 155                 160
        Val Val Thr Met Leu Val Leu Pro Ser Leu Gln Lys Ile Pro Glu Leu
                        165                 170                 175
        Ala Lys Leu Met Gly Ile Lys
                    180

<210> SEQ ID NO 12
<211> LENGTH: 418
<212> TYPE: PRT
<213> ORGANISM: Streptococcus suis
<220> FEATURE:
<221> NAME/KEY: SITE
<222> LOCATION: (1)..(418)
<223> OTHER INFORMATION: /note="ORF3 V10"

<400> SEQUENCE: 12

Met Asn Tyr Gln Glu Thr Arg Arg Trp Leu Ser Ser Arg Pro Ala Ser
 1               5                  10                  15

Asp Leu Glu Asn Gly Val Ala Arg Val Asn Trp Ile Leu Glu Arg Leu
             20                  25                  30

Asp Asn Pro Gln Leu Gln Val Pro Thr Val His Phe Val Gly Thr Asn
         35                  40                  45

Gly Lys Gly Ser Thr Leu Asn Ala Leu Gln Ser Ile Leu Gln Ser Ser
     50                  55                  60

Asp Tyr Thr Val Gly Arg Phe Thr Ser Pro Ser Ile Ile Asp Phe Arg
 65                  70                  75                  80

Glu Gln Ile Val Tyr Gln Gln Glu Met Ile Ser Glu Glu Asp Phe Ala
                 85                  90                  95

Arg Ile Val Thr Asp Leu Gln Pro Leu Ile Glu Asp Leu Asp Gln Thr
            100                 105                 110

Ala Gly Leu Asp Ala Ile Ser Glu Phe Glu Ile Val Val Val Ala Met
        115                 120                 125

Phe Val Tyr Phe Ala His Tyr Gln Arg Pro Asp Ile Leu Leu Val Glu
    130                 135                 140

Ala Gly Met Gly Gly Leu Gln Asp Ala Thr Asn Val Leu Ala Pro Leu
145                 150                 155                 160

Ala Val Val Cys Pro Ser Ile Gly Leu Asp His Gln Ala Phe Leu Gly
                165                 170                 175

Glu Thr His Ala Ala Ile Ala Arg His Lys Val Ala Val Leu Arg Glu
            180                 185                 190

Gly Val Pro Leu Ile Tyr Ala Thr Asp Gln Pro Glu Val Glu Thr Val
        195                 200                 205

Phe Glu Glu His Ala Cys Gln Leu Gln Ser Pro Thr Tyr Ala Val Gly
    210                 215                 220

Arg Glu Ile Leu Leu Glu Asn Ser Arg Ala Gly Phe Ala Val Ser Ser
225                 230                 235                 240

Pro Leu Gly Arg Val Glu Glu Leu Thr Leu Gln Met Gln Gly Arg His
                245                 250                 255

Gln Glu Val Asn Ala Ala Leu Ala Val Thr Thr Ala Gln Leu Ile Lys
            260                 265                 270

Pro His Phe Pro Thr Ile Thr Asn Glu Thr Ile Arg Gln Gly Leu Ser
        275                 280                 285

Gln Ala Ile Trp Pro Gly Arg Leu Glu Leu Ile Arg Pro Asn Leu Met
    290                 295                 300

Ile Asp Gly Ala His Asn Asn Glu Ser Ile Ala Val Leu Thr Gln Leu
305                 310                 315                 320
```

```
Leu Glu Glu Lys Tyr Ala Asp Arg Asp Ile Glu Ile Leu Phe Ala Ala
                325                 330                 335

Ile Asn Thr Lys Pro Val Asp Gln Met Leu Ser Gln Leu Ser Gln Phe
            340                 345                 350

Gly Pro Val Ser Val Thr Thr Phe Asp Phe Arg Ala Val Gln Leu
        355                 360                 365

Glu Asp Tyr Pro Ser Gly Tyr Glu Arg Val Gln Thr Tyr Gln Glu Trp
        370                 375                 380

Val Glu Gln Ala Asp Leu Asp Asn Pro Lys Lys Leu Tyr Leu Ile Thr
385                 390                 395                 400

Gly Ser Leu Tyr Phe Ile Thr Tyr Val Arg Lys Tyr Ile Leu Glu Glu
                405                 410                 415

Leu Val

<210> SEQ ID NO 13
<211> LENGTH: 418
<212> TYPE: PRT
<213> ORGANISM: Streptococcus suis
<220> FEATURE:
<221> NAME/KEY: SITE
<222> LOCATION: (1)..(418)
<223> OTHER INFORMATION: note="ORF3 V735"

<400> SEQUENCE: 13

Met Asn Tyr Gln Glu Thr Arg Arg Trp Leu Ser Ser Arg Pro Ala Ser
  1               5                  10                  15

Asp Leu Glu Asn Gly Val Ala Arg Val Asn Trp Ile Leu Glu Arg Leu
             20                  25                  30

Asp Asn Pro Gln Leu Gln Val Pro Thr Val His Phe Val Gly Thr Asn
         35                  40                  45

Gly Lys Gly Ser Thr Leu Asn Ala Leu Gln Ser Ile Leu Arg Ser Ser
     50                  55                  60

Asp Tyr Thr Val Gly Arg Phe Thr Ser Pro Ser Ile Ile Asp Phe Arg
 65                  70                  75                  80

Glu Gln Ile Val Phe Glu Gln Glu Met Ile Ser Glu Glu Asp Phe Ala
                 85                  90                  95

Arg Ile Val Thr Asp Leu Gln Pro Leu Ile Glu Asp Leu Asp Gln Thr
            100                 105                 110

Ala Gly Leu Asp Ala Ile Ser Glu Phe Glu Ile Val Val Ala Met
        115                 120                 125

Phe Val Tyr Phe Ala His Tyr Gln Arg Pro Asp Ile Leu Leu Val Glu
130                 135                 140

Ala Gly Met Gly Gly Leu Gln Asp Ala Thr Asn Val Leu Ala Pro Leu
145                 150                 155                 160

Ala Val Val Cys Pro Ser Ile Gly Leu Asp His Gln Ala Phe Leu Gly
                165                 170                 175

Glu Thr His Ala Ala Ile Ala Arg His Lys Val Ala Val Leu Arg Glu
            180                 185                 190

Arg Val Pro Leu Leu Tyr Ala Thr Asp Gln Ser Glu Val Val Ala Ala
        195                 200                 205

Phe Glu Asp His Ala Ser Gln Leu Gln Ser Pro Thr Tyr Ala Val Gly
    210                 215                 220

Arg Glu Ile Leu Leu Glu Asn Ser Arg Ala Gly Phe Ala Val Ser Ser
225                 230                 235                 240

Thr Leu Gly Arg Val Glu Glu Leu Thr Leu Gln Met Gln Gly Arg His
                245                 250                 255
```

```
Gln Glu Val Asn Ala Ala Leu Ala Val Thr Thr Ala Gln Leu Leu Ser
                260                 265                 270

Pro Asp Phe Pro Thr Ile Thr Asn Glu Thr Ile Arg Gln Gly Leu Ser
            275                 280                 285

Gln Ala Ile Trp Pro Gly Arg Leu Glu Leu Ile Arg Pro Asn Leu Met
        290                 295                 300

Ile Asp Gly Ala His Asn Asn Glu Ser Ile Ala Val Leu Thr Gln Leu
305                 310                 315                 320

Leu Glu Glu Lys Tyr Ala Asp Arg Asp Ile Glu Ile Leu Phe Ala Ala
                325                 330                 335

Ile Asn Thr Lys Pro Val Asp Gln Met Leu Ser Gln Leu Ser Gln Phe
            340                 345                 350

Gly Pro Val Ser Val Thr Thr Phe Asp Asp Phe Arg Ala Val Gln Leu
        355                 360                 365

Gly Asp Tyr Pro Ser Gly Tyr Glu Arg Val Gln Thr Tyr Gln Glu Trp
    370                 375                 380

Leu Glu Gln Val Asp Leu Asp Asn Pro Lys Gln Leu Tyr Leu Ile Thr
385                 390                 395                 400

Gly Ser Leu Tyr Phe Ile Thr Tyr Val Arg Lys Tyr Ile Leu Glu Glu
                405                 410                 415

Leu Val

<210> SEQ ID NO 14
<211> LENGTH: 2973
<212> TYPE: DNA
<213> ORGANISM: Streptococcus suis
<220> FEATURE:
<221> NAME/KEY: misc_feature
<222> LOCATION: (1)..(2973)
<223> OTHER INFORMATION: /note="V10 sequence fragment"

<400> SEQUENCE: 14
ggatcctgct atcattcctt atttgattgc gaatgttgaa gaactgaaag atgctgcaga      60
cgttgttaac atgttgaata aacagtcagg cttattcggt gtatctggct tctcaagtga     120
tatgcgtgat attgaagcag gtatccaagc tcacaatcca gatgcagtgt tggcctacaa     180
tattttcatt gaccgtatta agaaatttat cggtcagtat cttgcagttt taaatggggc     240
agatgctatt gtcttcaccg ctggtatggg tgaaaatgca ccgcttatgc gcaatgacgt     300
agtagaaggt tgtcttggt ttggtattga gttggaccta caaaaaaatg tattcggcaa     360
ctatggtgac atttcaacgg cagaatcaaa agttcgtgtc ttggttattc cgacggatga     420
agaattggtt attgcgcgtg aagtggaacg cttgaaataa gaaaaactaa ctggtagtcg     480
gagactgcca gttctctcta tagtttatac ctttagaaag gtatagtttt tagcaagtgg     540
acaaaatata tagtgtgtga tacaatagac tagcaaagaa atttgcacag agtagatggt     600
ttgcgtcaag tgtatgtgga tgggatgttg ccacataacg aagctgatct tgcttgcat      660 ctgatgtctc ctagagtagg aacattggtc ctggctgaga gtagcgcggt aaaccattgc     720
atccgctgtc gaatacacac gacagctcca tttttgaaa aaggagcatt ttttatggaa      780
aagaaaattc caaaactaac ggtgcagttg ttggctgcta ttgcgatgac ccttgccttg     840
gtcatgatta tagagaacta tttctctatt cggatttctg atactttaca ggttcagttt     900
accttcattc ccaatactat tttgggagct attgcgggtc agtttgggc agctgtcttt      960 gcggctattt cagacccagt ctttgtcttg tttagcgggc aaacggtcct cttcacttgg    1020
attttgattg aggcggtatc ggcatttatc tacggctggt tcttctatcg aaaaccgcta    1080
```

-continued

```
gacaccaaga acaaggctga ttggctctat gtggctggtg tagttgtctt gattcaggtt       1140
gtgatttcct ttatcatgac accgattgcc ctccatttcc attttggaac accttggatt       1200
gttctgtata gcagtcgctt gattaaggca gttttttgaaa ttccattacg cattgtcgtg      1260
accatgcttg tcttgccaag tttacaaaaa atacctgaat tggccaagtt aatgggcatt      1320
aaataaaaca gtatcaagca acaggtcatc cccctgttgc tacttttgta gagagggaat      1380
catgaattat caagaaactc gccggtggct atctagtcgt cctgcatcag atttagaaaa      1440
tggcgttgca cgtgtcaact ggattttaga acgcttggac aatccccagc ttcaagtgcc      1500
gaccgtacac tttgtgggca caaatggcaa gggctcgacc ctcaacgcct acagtctat       1560 cttgcagtct tcggattaca ccgtcggccg ctttacatca ccgtctatca ttgattttcg      1620
agagcagatt gtctaccagc aggagatgat ttcggaggaa gattttgcga ggattgtgac      1680
agacttgcaa cccttgatcg aggacttgga ccagacggct ggactggatg ccatctcgga      1740
gtttgagatt gtagtagtgg ctatgtttgt ctactttgcc cactaccagc gtcccgatat      1800
tctcttggtg gaggccggca tgggtggttt gcaggatgcg accaatgtcc ttgccccctt      1860
ggcagtagtt tgtccgtcca tcggtttgga ccatcaggca ttttttgggag agacccacgc     1920 tgctatagcc cgtcacaagg tcgccgtctt gcgtgagggg gttccgctca tctatgcgac      1980
cgaccagcca gaagtggaga cagtatttga ggagcatgcc tgtcagcttc agagtccgac      2040
ctatgcggtg gggcgggaga ttcttttgga aaatagcaga gcaggctttg cagtttcaag     2100
tcctctcggc cgtgtggaag agttaacact acagatgcag ggtcgtcacc aggaggtcaa      2160
tgcagccttg gcagtgacaa cagctcagct cattaaacct cattttccaa caattaccaa      2220
tgaaaccatc cgccagggct tgtcccaagc catctggccg ggtcgcttag agttgattag      2280
gcctaatctc atgattgacg gtgcccacaa taatgaaagt atcgccgtcc tgacacaact      2340
cttggaagaa aagtatgctg acagggatat tgaaatcctc tttgcggcca tcaataccaa      2400
gccagtggac cagatgttgt cccagcttag ccaatttgga cctgttagcg tgacgacctt      2460
tgacgatttc agagcggtac agttagaaga ttatccgtca ggctatgaac gagttcagac      2520
ctatcaggag tgggtggagc aggcggactt ggacaatccc aaaaaactct acctgattac      2580
aggctcgcta tatttcatta cctatgtgag gaagtacatt ttagaagaac ttgtttagaa      2640
aaaaaaggct ttgccgggca ttcaacccag caaagtcttt tgtttttaata attttttaatc   2700 aaatcaaccg ttgagcggtc tagtttttta acgatggtct gcaagaaggc ttgggcctct     2760
aagaagtcat cctatgctgta gagagtttga tgtgaatgga tgtagcgagc gcagacaccg     2820
atagttgttg atggaacacc atgatttttc aagtgggctg caccagcatc tgttccacct      2880
ttaccacagt agtattggaa tttgacacct gcttcttcgg cagttgtgag gaggaagtct     2940 ttcatgttttt ttaacatgat gtgacctgga tcc                                 2973
```

<210> SEQ ID NO 15
<211> LENGTH: 3098
<212> TYPE: DNA
<213> ORGANISM: Streptococcus suis
<220> FEATURE:
<221> NAME/KEY: misc_feature
<222> LOCATION: (1)..(3098)
<223> OTHER INFORMATION: /note="V735 sequence fragment"

<400> SEQUENCE: 15

```
ctgcagatgt tgtgaacatg ttgaataaac agtcaggctt gttcggtgta tctggcttct         60
caagtgatat gcgtgatatt gaagcaggca tccaagctca caatccagat gcagtgttgg        120
```

-continued

```
cctacaatat tttcattgac cgtattaaga aatttatcgg tcagtatctt gcagttttaa      180
atggggcaga tgctattgtc ttcacggctg gtatgggtga aaatgcaccg cttatgcgca      240
atgacgtagt agaaggcttg tcttggtttg gtattgagtt ggacccacaa aaaaatgtat      300
ttggcaacta tggtgacatt tcaacggcag aatcaagggt tcgtgtcttg gttattccga      360
cggatgaaga attggttatt gcgcgtgaag ttgaacgttt gaaataagaa aaactaactg      420
gtagtcggag actgccggtt tctcttatag tttataccgg tagaaaggta tagttttttag    480 caagtggtca aaatatatag tgtgtgatac aatagactag caaagaaatt tgcacagagt      540
agatggtttg cgtcaagtgt atgtggatgg gatgttgcca cataacgaag ctgatctttg      600
cttgcatctg atgtctccta gagtaggaac attggatctg gctgagagta gcgcggtaaa      660
ccattgcatc cgctgtcgaa tacacacgac agctccattt tttgaaaagg agcatttttt      720
atggaaaaga agattccaaa actaacggtg cagttgttgg ctgctattgc gatgactctt      780
gccttggtca tgattgcgga gaaccatttt tctgttcgtc tttctgatac cttgcaggtc      840
cagtttacct ttatccctaa tactatttta ggtgcgattg ctggtcctgt ttgggctgct      900
gtatttgcgg cgatttcaga cccagctttt gtcttgttta gtggacagag catgcttttt      960
agttttatct tgattgaggc ggtatcggct tttatctatg gctggttctt ctatcgaaaa      1020
ccgctagaca ccaagaacaa ggctgattgg ctctatgttg caggggttgt tgtcttgatt     1080
caggttgtga tttcctttat catgacaccg attgccctcc atttccattt tggaacacct     1140
tggattgttc tgtatagcag tcgcttgatt aaggcggttt ttgaaattcc attacgcatt     1200
gtcgtgacta tgcttgtctt accaagttta caaaaaatac ctgaattggc taagttaatg     1260
ggcattaaat aaaacagtat caagcaacag gtcatccccc tgttgctgct tttgtagaga     1320
gggaatcatg aattatcaag aaactcgccg gtggctatct agtcgtcctg catcagattt     1380
agaaaatggc gttgcacgtg tcaactggat tttggaacgc ttggacaatc cccagcttca     1440
agtgccgacc gttcacttcg taggtacaaa tggcaagggc tcgaccctca acgccttaca     1500
gtctatctta cggtcttcgg attacaccgt cggtcgcttt acctcaccgt ctatcattga     1560
ttttcgagag cagattgtat ttgagcagga gatgatttcg gaggaagatt ttgcaaggat     1620
tgtgacagac ttgcaaccct tgattgagga cttggaccag acggctggac tggatgccat     1680
ctcggagttt gagattgtag tagtggctat gtttgtctac tttgcccact accagcgtcc     1740
cgacattctc ttggtggagg cgggcatggg tggtttgcag gatgcgacca atgtccttgc     1800
cccattggca gtagtttgcc cgtccatcgg cttggaccat caggcttttt tgggagagac     1860
ccacgctgct atagcccgtc acaaggttgc tgtcttgcgt gagcgggttc ccctcctcta     1920
tgcgaccgac cagtcagaag tggtggcagc atttgaggat cacgccagtc agcttcagag     1980
tccgacctat gcggtgggac gggagattct tttggaaaat agcagagcag ctttgctgt      2040 ttcaagtact ctcggccgtg tggaagaatt aacactgcag atgcagggtc gtcaccagga     2100
ggtcaatgca gccttggcag tgacaacagc tcagcttctc agccctgatt ttccaacaat     2160
taccaatgaa accatccgcc agggcttgtc ccaagccatc tggccgggcc gcttagagtt     2220
gattaggcct aatctcatga ttgacggtgc ccacaataat gaaagtatcg ccgtcctgac     2280
acaactcttg gaagaaaagt atgctgacag ggatattgaa atcctctttg cggccatcaa     2340
taccaagcca gtggaccaga tgttgtccca gcttagccaa tttggacctg ttagcgtgac     2400
gacctttgac gatttcagag cggtacagtt aggagattat ccgtcaggct atgaacgagt     2460
tcagacctat caggagtggt tggagcaggt ggacttggac aatcccaaac aactctacct     2520
```

-continued

```
gattacaggc tcgctatatt tcattaccta tgtgaggaag tacattttag aagaacttgt    2580
atagaaaaaa ggctttgccg ggcattcaac ccagcaaagt cttttgtttt aataatttt     2640 aatcaaatca accgttgagc ggtctagttt tttaacgatg gtctgcaaga aggcttgggc    2700
ctctaagaag tcatccatgc tgtagagagt ttgatgtgaa tggatgtagc gagcgcagac    2760
accgatagtt gttgatggaa caccatggtt tttcaagtgg gctgcaccgg catctgttcc    2820
acctttacca cagtagtatt ggaatttgac acctgcttct tcggcagttg tgaggaggaa    2880
gtctttcatg tttttagca tgatgtggcc tgggtcatag aaacgaagca gagttccgtc     2940
accaattttt ccttggtcgc cataaatatc acctgcgggc gagcaatcaa cagcgaggaa    3000
aatgtctgga ttgaacttgg ttgtagaggc atgagcacca cgaagaccaa cctcttactt    3060
gcacattggc cccagcaatc aactgatttg caaagctt                            3098
```

VIRULENCE OF STREPTOCOCCI

CROSS-REFERENCE TO RELATED APPLICATIONS

This application is a continuation of U.S. patent application Ser. No. 11/499,884 filed Aug. 3, 2006, now U.S. Pat. No. 7,670,835 (Mar. 2, 2010), which is a continuation of U.S. patent application Ser. No. 10/435,654, filed May 9, 2003, now U.S. Pat. No. 7,109,006 (Sep. 19, 2006), which is a continuation of PCT/NL01/00805, filed Nov. 6, 2001, designating the United States of America, corresponding to PCT International Publication WO 02/38597 (published in English on May 16, 2002), which itself claims priority to EP 00203947, filed Jan. 15, 2004, the contents of each of which are incorporated herein in its entirety.

TECHNICAL FIELD

The invention relates generally to biotechnology, and, more particularly, to the diagnosis of and vaccination against Streptococcal infections and to the detection of virulence markers of Streptococci.

BACKGROUND

*Streptococcus* species, of which there are a large variety that cause infections in domestic animals and man, are often grouped according to Lancefield's groups. Typing, according to Lancefield, occurs on the basis of serological determinants or antigens that are, among others, present in the capsule of the bacterium and, thus, allows for an approximate determination. Often, bacteria from a different group show cross-reactivity with each other, while other Streptococci cannot be assigned a specific group-determinant at all. Within groups, further differentiation is often possible on the basis of serotyping. These serotypes further contribute to the large antigenic variability of Streptococci, a fact that creates an array of difficulties within diagnosis of and vaccination against Streptococcal infections.

Lancefield group A *Streptococcus* (GAS, *Streptococcus pyogenes*) are common with children and cause nasopharyngeal infections and complications thereof. Among animals, cattle are susceptible to GAS, and mastitis is often found.

Lancefield group B *Streptococcus* (GBS) are most often seen with cattle and cause mastitis. However, human infants are susceptible as well, often with fatal consequences. Group B streptococci (GBS) constitute a major cause of bacterial sepsis and meningitis among human neonates born in the United States and Western Europe and are emerging as significant neonatal pathogens in developing countries.

Lancefield group C infections, such as those with *S. equi, S. zooepidemicus, S. dysgalactiae*, and others are mainly seen with horse, cattle and pigs, but can also cross the species barrier to humans.

Lancefield group D (*S. bovis*) infections are found with all mammals and some birds, sometimes resulting in endocarditis or septicemia.

Lancefield groups E, G, L, P, U and V (*S. porcinus, S. canis, S. dysgalactiae*) are found with various hosts and cause neonatal infections, nasopharyngeal infections or mastitis.

Within Lancefield groups R, S, and T (and with ungrouped types), *S. suis* is found and is an important cause of meningitis, septicemia, arthritis and sudden death in young pigs. Incidentally, it can also cause meningitis in man.

Ungrouped *Streptococcus* species, such as *S. mutans*, causes caries with humans, *S. uberis*, causes mastitis with cattle, and *S. pneumonia*, causes major infections in humans, and *Enterococcus faecalis* and *E. faecium*, further contribute to the large group of Streptococci. *Streptococcus pneumoniae* (the pneumococcus) is a human pathogen that causes invasive diseases, such as pneumonia, bacteremia, and meningitis.

Little is known about the pathogenesis of the disease caused by Streptococci. Various cellular components, such as muramidase-released protein (MRP), extracellular factor (EF) and cell membrane-associated proteins, fimbriae, hemagglutinins, and hemolysin, have been suggested as virulence factors. However, the precise role of these protein components in the pathogenesis of the disease remains unclear. It is, however, known and generally accepted that the polysaccharidic capsule of various Streptococci and other gram-positive bacteria plays an important role in pathogenesis. The capsule enables these microorganisms to resist phagocytosis and is, therefore, regarded as an important virulence factor or marker.

In particular, *Streptococcus suis* is an important cause of meningitis, septicemia, arthritis and sudden death in young pigs. It can also cause meningitis in man. Attempts to control the disease are hampered by the lack of sufficient knowledge about the pathogenesis of the disease and the lack of effective vaccines and sensitive diagnostic methods.

So far, 35 serotypes of *S. suis* have been described. Virulence of *S. suis* can differ within and among serotypes. Worldwide, *S. suis* serotype 2 is the most frequently isolated serotype. Within *S. suis* serotype 2, pathogenic, weak-pathogenic and non-pathogenic strains can be found. The pathogenic strains cause severe clinical signs of disease in pigs and large numbers of bacteria can be re-isolated from the central nervous system (CNS) and the joints after experimental infection. The weak-pathogenic strains cause only mild clinical signs of disease and infrequently bacteria can be re-isolated from the CNS and the joints after experimental infection. The non-pathogenic strains are completely avirulent in young pigs after experimental infection.

The 136-kDa muramidase-related protein (MRP) and the 110-kDa extracellular factor (EF) are generally considered as important virulence markers for *S. suis* serotype 2 strains isolated in Europe and the United States. However, differences in virulence between pathogenic, weak-pathogenic and non-pathogenic strains cannot exclusively be explained by differences in their MRP and EF expression patterns. In addition, it is known that the capsule of *Streptococcus suis* serotype 2 is an important virulence factor. However, since pathogenic, weak-pathogenic and non-pathogenic strains seem to be fully encapsulated after growth in vitro and in vivo, it is not likely that the level of encapsulation of these fully encapsulated strains is associated with their difference in virulence.

SUMMARY OF THE INVENTION

Disclosed are methods for modulating virulence of a *Streptococcus* comprising modifying a genomic fragment of the *Streptococcus*, wherein the genomic fragment comprises at least a functional part of a fragment identifiable by hybridization in *Streptococcus suis* to a nucleic acid or fragment thereof as shown in FIG. 5. To gather an insight into the differences between pathogenic, weak-pathogenic and non-pathogenic strains that determine their difference in virulence, the invention discloses an in vivo complementation system wherein virulence can be modified by modifying the fragment.

For example, within *S. suis* serotype 2, pathogenic, weak-pathogenic and non-pathogenic strains are found. A genomic library of a pathogenic strain was introduced into a weak-pathogenic strain. After infection of the library into young piglets, pathogenic transformants were selected. One specific transformant that contained a 3 kb fragment of the pathogenic strain, V10, appeared to be dominantly enriched in diseased pigs. The observed enrichment was not tissue specific. The selected fragment, when introduced into two different weak-pathogenic strains, considerably increased the virulence of these strains. In particular, the fragment described and identified as ORF2, or functional fragments thereof, was shown to be an important virulence factor. In contrast, introduction of the corresponding fragment of a weak-pathogenic strain had only minor effects on virulence.

Accordingly, also described are methods for assaying virulence of a *Streptococcus* comprising assaying a genomic fragment of the *Streptococcus*, wherein the genomic fragment comprises at least a functional part of a fragment identifiable by hybridization in *Streptococcus suis* to a nucleic acid or fragment thereof as shown in FIG. 5, in particular the ORF2 fragment.

Nucleotide sequence analysis of the selected fragment of the pathogenic strain revealed the presence of two potential open reading frames, both of which were found to be mutated in the corresponding fragment of the weak-pathogenic strain. It was previously shown by ribotyping and random amplified polymorphic DNA analysis (RAPD) assays that pathogenic and weak-pathogenic strains of *S. suis* serotype 2 are genetically closely related, whereas non-pathogenic strains showed a high degree of genetic heterogeneity. A genomic library of the pathogenic *S. suis* strain 10 in plasmids was constructed and the plasmid library was introduced into the weak-pathogenic reference strain of *S. suis* serotype 2, strain S735. Pigs were inoculated intravenously with the recombinants and bacteria were recovered from the CNS and the joints of diseased pigs.

The re-isolated bacteria were subsequently analyzed for plasmid content and virulence. With this approach, a DNA fragment of a pathogenic serotype 2 strain that transformed weak-pathogenic strains into highly pathogenic strains was identified. This fragment, as described herein, comprises a genetic determinant important for virulence. The fragment is in other Streptococci identifiable by, for example, hybridization experiments such as Northern or Southern blotting, or by amplification experiments (such as PCR) using primers and/or probes derived from a nucleic acid as described herein.

With the fragment and parts thereof, such as the open reading frames identified in FIG. 3, a virulence marker is described herein. The marker is associated with an isolated and/or recombinant nucleic acid as described herein and derivable from *Streptococcus* and identifiable by hybridization in *Streptococcus* (preferably *S. suis*) to a nucleic acid or fragment thereof as shown in FIG. 5.

Also described are vectors comprising a nucleic acid according to the invention and a host cell comprising a nucleic acid or a vector according to the invention. Such a host cell comprises an easily modifiable organism such as *E. coli*. However, other host cells, such as recombinant *Streptococcus* (such as those derived from one of the grouped or ungrouped Streptococci as identified hereinabove) comprising a vector or nucleic acid according to the invention are also herein disclosed. In particular, recombinant *Streptococcus* as described herein is useful for inclusion in a vaccine.

Furthermore, also described are vaccines comprising a nucleic acid and a vector or a host cell according to the invention, and the use of such a vaccine in the prevention and/or treatment of Streptococcal infections.

Also described is a protein or fragment thereof encoded by a nucleic acid according to the invention, such as a protein encoded by ORF2 or ORF3 as disclosed herein, or a functional, i.e., antigenic fragment thereof. The invention also discloses an antibody directed against a protein or fragment thereof according to the invention and an antigen reactive with such an antibody, for example, comprising a protein or fragment. Such a protein or fragment thereof need not be obtained by recombinant means since synthesis of the peptides according to the amino acid sequence is also possible. Such antigens and antibodies as described herein can be used in a diagnostic test comprising an antibody of the invention, or within a vaccine or diagnostic test comprising the antigen of the invention. Such vaccines and diagnostic tests can be used in the field of diagnosis of and vaccination against Streptococcal infections and for the detection of virulence markers of Streptococci.

The phrase "means for imparting virulence" will be used to refer to a nucleic acid that encodes a peptide corresponding to a virulence factor or to a peptide encoded by the nucleic acid that possesses a characteristic associated with the virulence factor. The phrase "means for imparting virulence" also includes, without limitation, the nucleic acids having sequences corresponding to SEQ ID NO:14 and SEQ ID NO:15, and the peptides having sequences corresponding to SEQ ID NOS:10-13, and any functional sequences originating therefrom. For instance, the nucleic acid sequence and the amino acid sequence may have conservative changes, such as additions, deletions or substitutions that do not affect a function associated with the virulence factor. For example, since the genetic code is degenerate, i.e., an amino acid may be encoded for by more than one codon, a conservative change in an original nucleic acid may result in an altered nucleic acid that encodes the same or homologous peptide as the original nucleic acid, wherein the peptide encoded by the altered nucleic acid retains the same function as the original nucleic acid. Further, since some amino acids are similar in charge, a conservative change, such as an addition, deletion or substitution, in the original amino acid sequence may result in an altered amino acid sequence, wherein the altered amino acid sequence retains the same function as the original amino acid sequence.

BRIEF DESCRIPTION OF THE DRAWINGS

FIG. 1 depicts the pCOM1 vector. pCOM1 contains the replication functions of pWVO1, the erythromycin-resistance gene of pE194 preceded by the promoter region of the mrp gene, as well as the SacI-PstI part of the multiple cloning site of pKUN19.

FIG. 2 shows plasmids digested with SmaI and XbaI on an 0.8% agarose gel. Library: plasmids isolated from ten randomly selected clones of the original library; clones enriched in pigs: plasmids isolated from 19 independently selected clones enriched in pigs; c: pCOM1; m: molecular size marker.

FIG. 3 is a schematic representation of the fragments V10 and V735. The arrows indicate the potential ORFs. œ P, indicates the position of the potential promoter sequence; °, indicates the positions of the potential transcription regulator sequences. Homologies (% identities) between the potential proteins encoded by the ORFs and proteins present in the data libraries are indicated.

FIGS. 4A and 4B illustrate the homology between the ORFs 2 (A) and 3 (B) encoding proteins of fragments V10 and V735. The asterisks indicate the nonidentical amino acids.

FIGS. 5A-5F are nucleotide and amino acid sequences of fragments V10 and V735.

DETAILED DESCRIPTION

Bacterial strains and growth conditions. The bacterial strains and plasmids used herein are listed in Table 1. *S. suis* strains were grown in Todd-Hewitt broth (code CM189, Oxoid) and plated on Columbia agar blood base (code CM331, Oxoid) containing 6% (v/v) horse blood. If required, antibiotics were added at the following concentrations: erythromycin, 1 μg/ml. E. coli strains were grown in Luria broth and plated on Luria broth containing 1.5% (w/v) agar. If required, 200 μg/ml of erythromycin was added.

pCOM1. pCOM1 (FIG. 1) is based on the replication functions of pWVO1. Further, the vector contained the erythromycin-resistance gene of pE194 preceded by the promoter region of the mrp gene, as well as the SacI-PstI part of the multiple cloning site of pKUN19. As a result, pCOM1 contained a unique BamHI site (FIG. 1).

Construction of the genomic S. suis library in pCOM1. Sau3AI partial digests of the DNA of the pathogenic S. suis serotype 2, strain 10 were size fractionated (>3 kb) by precipitation with 4.6% of PEG 6000 (BDH Chemicals, 19). The fragments were ligated to BamHI-digested pCOM1 and the ligation mixtures were transformed to E. coli XL2-blue cells. Erythromycin-resistant colonies were selected. About 17,000 independent E. coli clones were obtained. Analysis of 55 of the transformants showed that 64% contained an insert of greater than 3 kb. From the pool of E. coli transformants, plasmid DNA was isolated and subsequently used for the electrotransformation of the weak-pathogenic S. suis strain S735. This resulted in approximately 30,000 independent S. suis transformants. The S. suis library was designated S735 (pCOM-L). The transformants were pooled and stored at −80° C.

DNA techniques. Routine DNA manipulations were performed as described by Sambrook et al. DNA sequences were determined on a 373A DNA Sequencing System (Applied Biosystems, Warrington, GB). Samples were prepared by use of an ABI/PRISM dye terminator cycle sequencing-ready reaction kit (Applied Biosystems). Custom-made sequencing primers were purchased from Life Technologies. Sequencing data was assembled and analyzed using the McMollyTetra software package. The BLAST program was used to search for protein sequences homologous to the deduced amino acid sequences.

For PCR reaction mixtures (50 μl), the PCR Expand High Fidelity system (Boehringer, Mannheim, Germany) was used as described by the supplier. DNA amplification was carried out in a Perkin Elmer 9600 thermal cycler and the program included an incubation for two minutes at 95° C., ten cycles of 20 seconds at 95° C., one minute at 60° C. and four minutes at 68° C., 30 cycles of 20 seconds at 95° C., one minute at 60° C. and four minutes, extended with 20 seconds for each cycle, at 68° C. and ten minutes at 72° C.

Southern blotting and hybridization. Chromosomal DNA was isolated as described by Sambrook et al. DNA fragments were separated on 0.8% agarose gels and transferred to Gene-Screen Plus membranes (NEN) as described by Sambrook et al. DNA probes were labeled with [($\alpha$-$^{32}$P)dCTP (3000 Ci mmol$^{-1}$; Amersham) by use of a random primed labeling kit (Boehringer). The DNA on the blots was hybridized at 65° C. with the appropriate DNA probes as recommended by the supplier of the Gene-Screen Plus membranes. After hybridization, the membranes were washed twice with a solution of 40 mM sodium phosphate, pH 7.2, 1 mM EDTA, 5% SDS for 30 minutes at 65° C., and twice with a solution of 40 mM sodium phosphate, pH 7.2, 1 mM EDTA, 1% SDS for 30 minutes at 65° C.

Construction of pCOM-V10-ORF2 and pCOM-V10-ORF3. To construct pCOM-V10-ORF2, the primers 5'-CGAGCTCGGAAGAATTGGTTATTGCGCGTG-3' (SEQ ID NO:1) and 5'-CGGGATCCCGGGGGATGACCT-GTTGCTTG-3' (SEQ ID NO:2) were used in a PCR reaction on chromosomal DNA of S. suis strain 10 to amplify the ORF2 encoding region. The resulting fragment was purified, digested with SacI and BamHI and cloned into SacI and BamHI-digested pCOM1.

To construct pCOM-V10-ORF3, the primers 5'-TC-CCCCGGGGGACAAGCAACGGGTCATCCCC-3' (SEQ ID NO:3) and 5'-CGGGATCCCGGTTGAATGCCCG-GCAAAGCG-3' (SEQ ID NO:4) were used to amplify the ORF3 encoding region. The resulting fragment was digested with SmaI and BamHI and cloned into pKUN19. The resulting plasmid was designated pKUN-ORF3. Because the ORF2 and ORF3 encoding regions are most probably co-transcribed, the promoter region of ORF2 was subsequently amplified with primers 5'-CGAGCTCGGAAGAATTGGT-TATTGCGCGTG-3' (SEQ ID NO:1) and 5'-TC-CCCCGGGGGAGTCGTGTGTATTCGACAGCGG-3' (SEQ ID NO:5). The fragments were digested with SacI and SmaI and cloned into SacI and SmaI-digested pKUN-ORF3. The resulting plasmid was digested with SacI and BamHI, and the insert fragment was purified and cloned into SacI and BamHI-digested pCOM1. This resulted in pCOM-V10-ORF3.

Experimental infections. Germfree pigs, crossbreeds of Great Yorkshire and Dutch landrace, were obtained from sows by caesarian sections. The surgery was performed in sterile flexible film isolators. Pigs were allotted to groups, each including 4 or 5 pigs, and were housed in sterile stainless-steel incubators. Housing conditions and feeding regimes were performed as described by Vecht et al. One-week-old pigs were intravenously inoculated with S. suis strains as described by Vecht et al. Pigs received erythromycin orally twice a day (Erythromycin stearate, Abbott B. V., Amstelveen, The Netherlands, 40 mg/kg body weight). Two hours after the infection, the pigs were treated with erythromycin for the first time. Pigs were monitored twice a day for clinical signs of disease, such as fever, nervous signs and lameness. Blood samples were collected three times a week from each pig. White blood cells were counted with a cell counter.

To monitor infection with S. suis, swabs of nasopharynx and feces were collected daily. The swabs were directly plated onto Columbia agar containing 6% horse blood. After the pigs were sacrificed, they were examined for pathological changes. Further, tissue specimens were collected from the central nervous system, serosa, joints, lungs, liver, kidney, spleen, heart and tonsils. The tissues were homogenized in the presence of Todd-Hewitt medium by using an Ultra-Turrax tissuemizer (Omni International, Waterbury, USA), centrifuged for five minutes at 3,000 rpm and the supernatants were frozen at −80° C. in the presence of 15% glycerol.

Results.

Complementation system. A genomic library of the pathogenic S. suis strain 10 was constructed into the weak-pathogenic strain S735 as described in Materials and Methods. The plasmid pCOM1 allowed the insertion of large DNA fragments into the unique BamHI site (FIG. 1). The plasmid carries the origin of replication of pWVO1 that functions in E. coli and in S. suis. This allowed the construction of a DNA library in E. coli first. Plasmid DNA, isolated from the pool of E. coli transformants, was subsequently electrotransformed into S. suis strain S735. 30,000 individual S. suis clones were obtained. As determined by analysis of 24 randomly selected transformants, more than 30% of the S735 (pCOM-L) transformants contained an insert greater than 3 kb.

Selection of genomic fragments associated with virulence. To select for genetic determinants of the pathogenic S. suis strain 10 that could increase the virulence of the weak-pathogenic strain S735, pigs were inoculated with the *S. suis* library S735 (pCOM-L). A dose of either $10^7$ or $10^8$ cfu was used and the pigs were treated with erythromycin as described in Materials and Methods. All pigs showed specific *S. suis* symptoms (Table 2, A) three to seven days after the infection and, except for one, all pigs died during the course of the experiment. From five of the pigs, bacteria could be re-isolated from the CNS, and from two other pigs, bacteria were isolated from the joints (Table 2, A).

Figure 2:
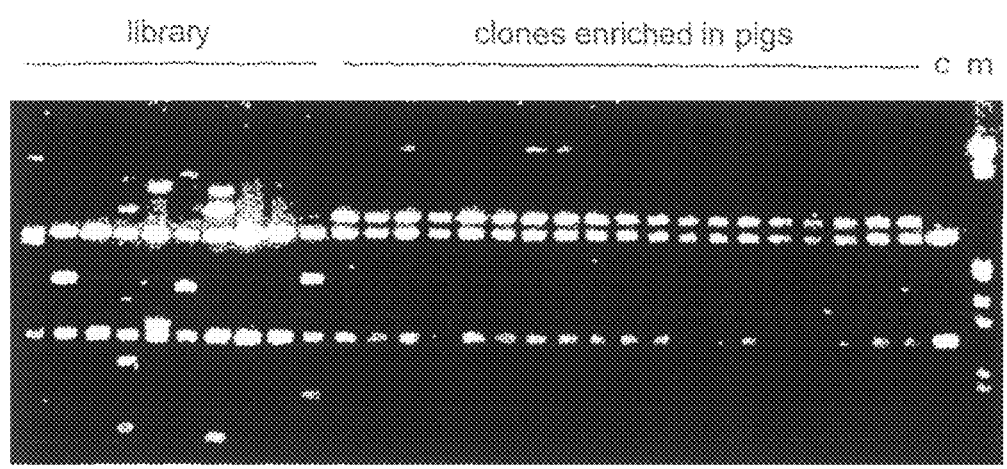
Figure 3:
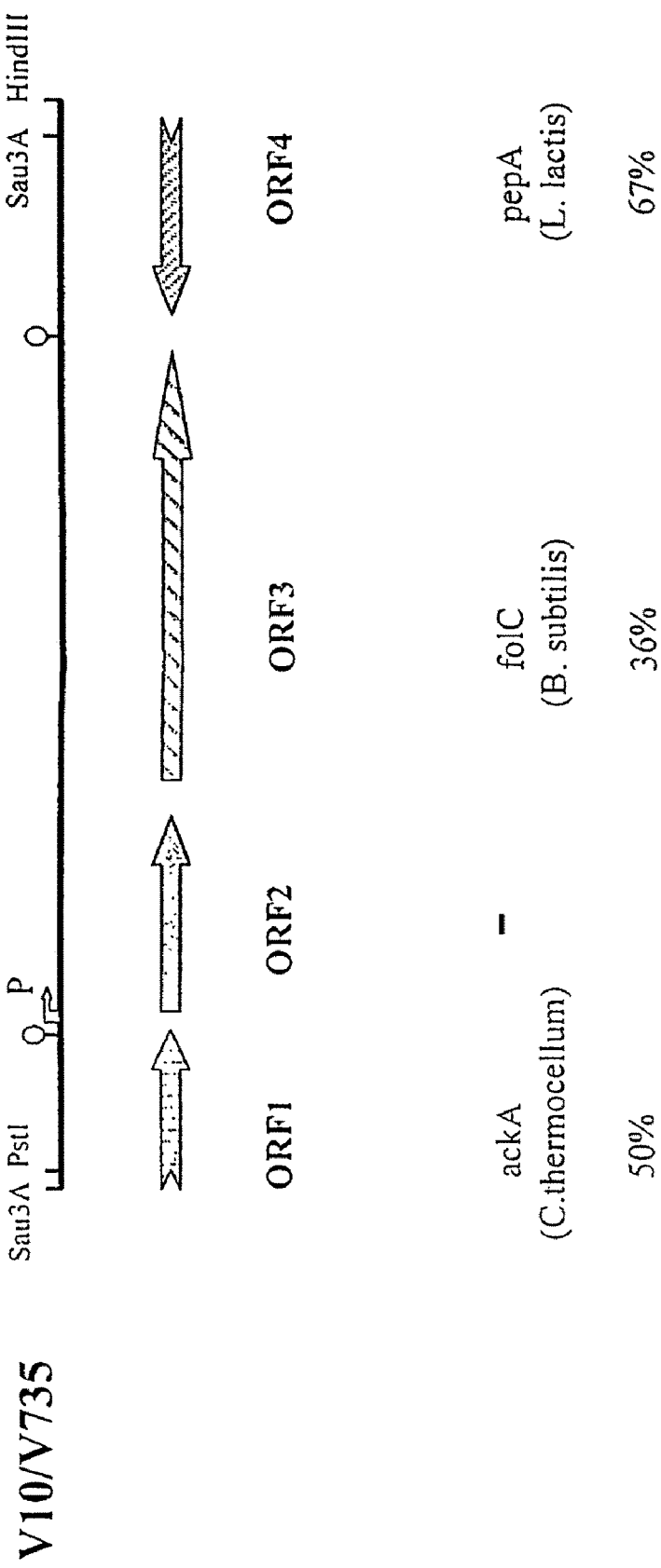

In previously performed experiments in which pigs were inoculated with weak-pathogenic strains, specific *S. suis* symptoms were observed with a very low frequency. In addition, from those pigs, bacteria could not be re-isolated from the CNS or from the joints. Therefore, the data indicated that, compared to virulence of strain S735, bacteria isolated from pigs inoculated with the *S. suis* library S735 (pCOM-L) are more virulent due to the presence of a DNA fragment of the pathogenic strain 10. The plasmid content of 90 randomly selected clones isolated from the CNS or the joints of the seven diseased pigs was analyzed by PCR and restriction analysis. The results showed that 88 of the 90 clones analyzed (19 of which are shown in FIG. 2) contained an insert of about 3 kb and had substantially identical restriction patterns. Moreover, the inserts of ten randomly selected clones having substantially identical restriction patterns also showed identical DNA sequences (results not shown). Plasmid DNA of ten randomly selected clones from the original S735 (pCOM-L) library showed ten different restriction patterns (FIG. 2). The data suggest that one specific clone, which was designated S735 (pCOM-V10), was greatly enriched in seven different pigs. Further, this particular clone was isolated from the CNS and from the joints of the various pigs, indicating that the observed enrichment was not tissue specific.

Virulence-associated properties of the selected fragment V10. To further analyze the virulence properties of strain S735 (pCOM-V10), pigs were intravenously inoculated with $10^6$ cfu of strain S735 (pCOM1) or strain S735 (pCOM-V10). The results (Table 2, B) show that, compared to the virulence of strain S735 (pCOM1), the virulence of strain S735 (pCOM-V10) was greatly enhanced.

All pigs inoculated with strain S735 (pCOM-V10) showed specific *S. suis* symptoms and died within one day after infection. In contrast, except for one, none of the pigs inoculated with the control strain S735 (pCOM1) showed specific clinical symptoms and these pigs survived until the end of the experiment (15 days after infection). The data proved that introduction of fragment V10 of strain 10 into S735 transformed the weak-pathogenic strain S735 into a highly pathogenic strain. This strongly suggests that the protein(s) encoded by V10 are important virulence determinants and play an important role in the pathogenesis of *S. suis* serotype 2 infections in pigs.

To find out whether the observed increase of the fragment V10 on virulence was specific for strain S735, pCOM1 and pCOM-V10 were introduced into another weak-pathogenic strain, strain 24. Subsequently, the virulence properties of the strains 24 (pCOM1) and 24 (pCOM-V10) were determined. As shown in Table 2 C and D, similar effects of V10 on the virulence of strains S735 and 24 were observed. Both strains 24 (pCOM-V10) and S735 (pCOM-V10) were highly pathogenic for young piglets, whereas strains 24 (pCOM1) and S735 (pCOM1) were shown to be weakly-pathogenic (Table 2, C and D). This strongly indicates that V10 has a more general ability to transform weak-pathogenic serotype 2 strains into highly pathogenic strains.

Because a plasmid system for the complementation approach was used, gene-dose effects cannot be excluded. Plasmid pCOM1 is based on the replication functions of pWVO1. In Gram-positive bacteria, the latter plasmid has a copy number of between 3 and 6. To find out whether copy effects play a role, the genomic region of strain S735 homologous to fragment V10 of strain 10 (see below) was cloned into plasmid pCOM1. This plasmid was designated pCOM-V735. The virulence of strains S735 (pCOM-V735), and 24 (pCOM-V735) was subsequently compared to that of S735 (pCOM-V10), S735 (pCOM1), 24 (pCOM-V10) and 24 (pCOM1). The results (Table 2, C and D) show that, in contrast to pCOM-V10, the plasmid pCOM-V735 did not carry virulence-enhancing activity. Pigs infected with strains S735 (pCOM-V10) and 24 (pCOM-V10) died within one or two days after infection, whereas most of the pigs infected with strains S735 (pCOM-V735), 24 (pCOM-V735), S735 (pCOM1) and 24 (pCOM1) survived until the end of the experiment (17 days after infection).

Compared to pigs infected with strains containing pCOM1, pigs infected with strains containing pCOM-V735 developed more general and specific signs of disease, but much less than pigs infected with strains containing pCOM-V10 (Table 2, C and D). From these data, it was concluded that the differences in virulence observed between the strains containing pCOM-V10 and the strains containing pCOM-VS735 are caused by differences between the fragments V10 and V735 (see below). The differences in virulence observed between the strains containing pCOM1 and the strains containing pCOM-VS735 may be due to gene-dose effects.

Sequence analysis of fragments V10 and V735. By using the fragment V10 as a probe, a 3.1 kb PstI-HindIII fragment of strain S735 (V735) was identified and cloned into pCOM1 (FIG. 3). To analyze the differences between the fragments V10 and V735, the nucleotide sequences of the fragments V10 and V735 were determined and the sequences were analyzed for homology to known genes by comparison with the GenBank/EMBL and SWISSPROT databases.

The sequence of V10 revealed two complete and two incomplete open reading frames (FIG. 3). ORF1 (nucleotides 1 to 461) coded for a polypeptide of 153 amino acids. This protein showed homology (49% identity) to the C-terminal region of acetate kinase of *Clostridium thermocellum* (accession number AF041841) and various other bacterial species. ORF2 (nucleotides 625 to 1327) coded for a protein of 233 amino acids. No significant similarities were found between the predicted amino acid sequence of this protein and other proteins present in the data libraries.

ORF3 (nucleotides 1382 to 2639) coded for a protein of 418 amino acids. This protein showed homology (36% identity) to FolC (folylpolyglutamate synthetase) of *Bacillus subtilis*. Compared to the other ORFs, ORF4 is transcribed in the opposite direction. ORF4 (nucleotides 2684 to 2972) coded for a polypeptide of 96 amino acids. This polypeptide showed homology (67% identity) to the C-terminal part of PepA (glutamyl-aminopeptidase) of *Lactococcus lactis*. Both ORFs 2 and 3 possessed putative initiation codons and ribosome-binding sites. Putative −35 (TGGACA) and −10 (TACAAT) sequences, which may function as promoter sequences, were found preceding ORF2. ORFs 2 and 3 were separated by 55 nucleotides. In this region, no putative promoter sequences could be observed. This could indicate that the ORFs 2 and 3 are co-transcribed. Downstream of the ORFs 1 and 3, regions of extended dyad symmetry were found which may function as transcription termination signals.

The sequence of the fragment V735 was determined and compared to the sequence of the fragment V10. No major deletions or insertions were found between the sequenced regions. The ORFs 1, 3 and 4 of strains 10 and S735 were highly homologous. The putative protein fragments encoded by the ORFs 1 differed in 2 (1.3%) amino acids; the putative proteins encoded by the ORFs 3 differed in 19 (4.5%) amino acids (FIG. 4B), whereas the putative protein fragments of the ORFs 4 were identical. However, major differences were observed between the ORFs 2 of strains 10 and S735. In the pathogenic strain 10, an ORF of 699 bases was found with a protein product of 233 amino acids. In contrast, due to a frame-shift mutation in the weak-pathogenic strain S735, an ORF of 569 bases was found and coded for a polypeptide of 183 amino acids.

Compared to the putative protein encoded by strain 10, the putative protein encoded by strain S735 lacked the N-terminal 50 amino acids (FIG. 4A). Besides these N-terminal differences, the putative proteins differed at 9 amino acid positions (4.9%). In addition, the putative −35 regions that may be part of the promoter sequences involved in the expression of ORFs 2 and 3 differed between the two strains. A TGGACA sequence was found in strain 10, whereas a TGGTCA sequence was found in strain S735. The sequence data suggest that the differences in the virulence-enhancing effects of the fragments V10 and V735 may be the result of functional differences between the putative proteins expressed by the ORFs 2 and/or 3, and/or by differences in their levels of expression.

ORF2 or ORF3.

To examine whether the observed increase of the fragment V10 on virulence resulted from ORF2 or ORF3 or both, the plasmids pCOM-V10-ORF2 and pCOM-V10 ORF3 containing the individual ORF2 and ORF3 encoding regions were constructed. Because ORF3 is probably co-transcribed with ORF2, in pCOM-V10-ORF3 the ORF3 encoding region was preceded by the promoter region of ORF2. Subsequently, the virulence properties of the strains S735 (pCOM-V10), S735 (pCOM-V10-ORF2), S735 (pCOM-V10-ORF3) and S735 (pCOM1) were determined. As shown at E in Table 2, the fragments V10 and ORF2 showed similar effects on the virulence of strain S735 while no effect of ORF 3 could be observed on the virulence of strain S735. These data show that ORF2 is responsible for the observed effect on virulence and that the ORF2 protein is an important virulence factor.

Distribution of the ORF2 and ORF3 sequences among all known 35 *S. suis* serotypes. To examine the homology between the ORF2 and ORF3 genes and genes of other *S. suis* serotypes, cross-hybridization experiments were performed. DNA fragments of the ORF2 and 3 genes were amplified by PCR, labeled by $^{32}$P, and hybridized to chromosomal DNAs of the reference strains of the 35 different *S. suis* serotypes. As a positive control, a probe specific for 16S rRNA was used. The 16S rRNA probe hybridized with almost equal intensities with all serotypes tested (results not shown). Probes ORF2 and ORF3 hybridized with all serotypes, except for serotypes 32 and 34 (results not shown). This indicates that the proteins encoded by ORF2 and 3 are common among most *Streptococcus* species.

Herein, the development and the successful application of an in vivo complementation approach for the identification of important molecular determinants that determine the differences in virulence between pathogenic and weak-pathogenic strains of *Streptococcus* is described. Using the complementation approach, one unique clone containing a 3.0 kb fragment of pathogenic strain (V10) was selected. The selected fragment was greatly enriched in seven different pigs and the observed enrichment was not tissue specific. The selected fragment showed similar enhancing effects on the virulence of two different weak-pathogenic strains. Large differences were observed between the effects of the selected fragment V10 of the pathogenic strain 10 and the corresponding fragment V735 isolated from the weak-pathogenic strain S735 on virulence.

In contrast to V10, which had a strong virulence-enhancing effect on weak-pathogenic strains, V735 showed only minor effects. Therefore, differences between these two fragments are considered responsible for the observed differences on virulence. Sequence data showed that the fragments V10 and V735 were highly homologous. Both fragments contained two complete ORFs (ORFs 2 and 3), both of which can potentially express proteins that may further contribute to the observed effect on virulence. The ORFs 3 are highly homologous and differ in only 19 amino acids.

The proteins encoded by the ORFs 3 showed homology to FolC (folylpolyglutamate synthetase) of various pro- and eukaryotic organisms. Folylpolyglutamate synthetase catalyzes the conversion of folates to polyglutamate derivatives. Bacteria require folates for the biosynthesis of glycin, methionine, formylmethionine, thymidine, purines and pantothenate. Whether the FolC proteins encoded by the fragments V10 and V735 have different enzymatic activities or different substrate specificities is unknown so far. In *E. coli*, an folC mutant is methionine deficient; however, so far, a role of FolC in virulence has not been described. Significant differences were also observed between the ORFs 2 of the fragments V10 and V735. Compared to the putative ORF2 protein encoded by strain 10, the putative protein encoded by strain S735 lacked the N-terminal 50 amino acids. In strain S735, a strong ribosome-binding site precedes the methionine start codon of ORF2. In contrast, however, the sequence in strain 10 did not indicate the presence of a strong ribosome-binding site preceding the methionine start codon of ORF2. Therefore, although ORF2 of strain 10 is extended compared to ORF2 of strain S735, it is not clear whether the proteins expressed by these two ORFs differ in length.

In addition to the putative N-terminal differences, the putative ORF2 proteins differed at nine amino acid positions (4.9%). Except for one amino acid, these amino acid substitutions were clustered at two different positions in the putative protein. The function of the ORF2 protein is unknown so far. Not even distant or partial homologies were found between the ORF2 protein sequences and protein sequences present in the data libraries. Hydrophobicity profiles showed that the ORF2-encoded protein(s) are very hydrophobic, thus suggesting a role of the ORF2 protein in the cellular membrane. The putative −35 region preceding the ORFs 2 and 3 differed between strains S735 and 10. Therefore, differences in the expression levels rather than functional differences responsible for the observed effects on virulence are not excluded.

In previous experiments, it was found that pigs infected with weak-pathogenic strains showed only mild clinical signs of disease and that bacteria could never be re-isolated from the CNS or the joints. Surprisingly, in the experiments described herein in which weak-pathogenic strains containing the control plasmid pCOM1 were used, bacteria could (with a low frequency) be re-isolated from the CNS as well as from the joints. Several possible explanations for these observed differences exist. One explanation is that the presence of the plasmid somehow affects the (virulence) properties of the strains. Another possibility is that the treatment of the pigs with erythromycin makes the pigs more sensitive for *S. suis* infections, and a third possibility is that, compared to the pigs previously used, the pigs used for the current experiments were more sensitive for *S. suis* infections.

REFERENCES

Anson K. J., S. Movahedi, H. G. Griffin, M. J. Gasson and F. Mulholland. 1995. A non-essential glutamyl aminopeptidase is required for optimal growth of *Lactococcus lactis* MG1363 in milk. *Microbiol.* 141:2873-2881.

Arends J. P. and H. C. Zanen. 1988. Meningitis caused by *Streptococcus suis* in humans. *Rev. Infect. Dis.* 10:131-137.

Awad-Masalmeh M., J. Köfer, M. Schuh and F. Hinterdorfer. 1999. Serotypen, virulenzfaktoren und empfindlichkeit gegenuber antibiotika von *Streptococcus suis* stämmer isoliert aus klinisch gesunden und erkrankten schweinen in Österreich. Wien. *Tierärtztl. Mschr.* 86:262-269.

Bogner A. L., C. Osborne and B. Shane. 1987. Primary structure of the *Escherichia coli* folC gene and its folylpolyglutamate synthetase-dihydrofolate synthetase product and regulation of expression by an upstream gene. *J. Biol. Chem.* 262:12337-12343.

Chalettier S., M. Gottschalk, R. Higgins, R. Brousseau and J. Harel. 1999. Relatedness of *Streptococcus suis* serotype 2 isolates from different geographic origins as evaluated by molecular fingerprinting and phenotyping. *J. Clin. Microbiol.* 37:362-366.

Clifton-Hadley F. A. 1983. *Streptococcus suis* type 2 infections. *Br. Vet. J.* 139:1-5.

Galina L., U. Vecht, H. J. Wisselink and C. Pijoan. 1996. Prevalence of various phenotypes of *Streptococcus suis* isolated from swine in the USA based on the presence of muramidase-released protein and extracellular factor. *Can. J. Vet. Res.* 60:72-74.8.

Gottschalk M., R. Higgins, M. Jacques, R. K. Mittal and J. Henrichsen. 1989. Description of 14 new capsular types of *Streptococcus suis. J. Clin. Microbiol.* 27:2633-2636.

Gottschalk M., R. Higgins, M. Jacques, M. Beaudain and J. Henrichsen. 1991. Characterization of six new capsular types (23-28) of *Streptococcus suis. J. Clin. Microbiol.* 29:2590-2594.

Higgins R., M. Gottschalk, M. Jacques, M. Beaudain and J. Henrichsen. 1995. Description of six new capsular types (29-34) of *Streptococcus suis. J. Vet. Diagn. Invest.* 7:405-406.

Horinouchi S, and B. Weisblum. Nucleotide sequence and functional map of pE194, a plasmid that specifies inducible resistance to macrolide, lincosamide and streptogramin type B antibiotics. *J. Bacteriol.* 150:804-814.

Kakuda H., K. Honoso, K. Shiroishi and S. Ichihara. 1994. Identification and characterization of the ack (acetate kinase A)-pta (phosphotransacetylase) operon and complementation analysis of acetate utilization by an ackA-pta deletion mutant of *Escherichia coli. J. Biochem.* 116:916-922.

Kok J., J. M. B. M. van der Vossen and G. Venema. 1984. Construction of plasmid cloning vectors for lactic acid streptococci which also replicate in *Bacillus subtilis* and *Escherichia coli. Appl. Environ. Microbiol.* 48:726-731.

Konings R. N. H., E. J. M. Verhoeven and B. P. H. Peeters. 1987. pKUN vectors for the separate production of both DNA strands of recombinant plasmids. *Methods Enzymol.* 153:12-34.

Luo D., J. Leautey, M. Grunberg-Manago and H. Putzer. 1997. Structure and regulation of expression of the *Bacillus subtilis* valyl-tRNA synthetase gene. *J. Bacteriol.* 179:2472-2478.

Luque I., C. Tarradas, R. Astorga, A. Perea, H. J. Wisselink and U. Vecht. 1998. The presence of muramidase released protein and extracellular factor protein in various serotype of *Streptococcus suis* isolated from diseased and healthy pigs in Spain. *Res. Vet. Science* 66:69-72.

Margolis P. S., A. Driks and R. Losick. 1993. Sporulation gene spoIIB from *Bacillus subtilis. J. Bacteriol.* 175:528-540.

Miller J. 1972. *Experiments in molecular genetics.* Cold Spring Harbor Laboratory, Cold Spring Harbor, N.Y.

Paithankar K. R. and K. S. N. Prasad. 1991. Precipitation of DNA by polyethylene glycol and ethanol. *Nucleic Acids Res.* 19:134.

Sambrook J., E. F. Fritsch and T. Maniatis. 1989. *Molecular cloning: a laboratory manual,* 2nd ed. Cold Spring Harbor Laboratory Press, Cold Spring Harbor, N.Y.

Salasia S. I. O. and C. Lämmler. 1995. Distribution of serotype, virulence markers and further characteristics of *Streptococcus suis* isolates from pigs. *J. Vet. Med. Series B* 42:78-83.

Smith H. E., M. Damman, J. van der Velde, F. Wagenaar, H. J. Wisselink, N. Stockhofe-Zurwieden and M. A. Smits. 1999. Identification and characterization of the cps locus of *Streptococcus suis* serotype 2: the capsule protects against phagocytosis and is an important virulence factor. *Infect. Immun.* 67:1750-1756.

Smith H. E., M. Rijnsburger, N. Stockhofe-Zurwieden, H. J. Wisselink, U. Vecht and M. A. Smits. 1997. Virulent strains of *Streptococcus suis* serotype 2 and highly virulent strains of *Streptococcus suis* serotype 1 can be recognized by a unique ribotype profile. *J. Clin. Microbiol.* 35:1049-1053.

Smith H. E., U. Vecht, A. L. J. Gielkens and M. A. Smits. 1992. Cloning and nucleotide sequence of the gene encoding the 136-kilodalton surface protein (muramidase-released protein) of *Streptococcus suis* type 2. *Infect. Immun.* 60:2361-2367.

Smith H. E., U. Vecht, H. J. Wisselink, N. Stockhofe-Zurwieden, Y. Biermann, and M. A. Smits. 1996. Mutants of *Streptococcus suis* types 1 and 2 impaired in expression of muramidase-released protein and extracellular protein induce disease in newborn germfree pigs. *Infect. Immun.* 64:4409-4412.

Smith, H. E., H. J. Wisselink, U. Vecht, A. L. J. Gielkens, and M. A. Smits. 1995. High-efficiency transformation and gene inactivation in *Streptococcus suis* type 2. *Microbiol.* 141:181-188.

Staats J. J., B. L. Plattner, G. C. Stewart and M. M. Chengappa. 1999. Presence of the *Streptococcus suis* suilysin gene and expression of MRP and EF correlates with high virulence in *Streptococcus suis* type 2 isolates. 1999. *Vet. Microbiol.* 70:201-211.

Stockhofe-Zurwieden N., U. Vecht, H. J. Wisselink, H. van Lieshout, and H. E. Smith. 1996. Comparative studies on the pathogenicity of different *Streptococcus suis* serotype 1 strains, p. 299. In P. G. Monetti and G. Vignola (ed.), Proceedings of the 14th International Pig Veterinary Society Congress, Bologna, Italy.

Vecht U., J. P. Arenda, E. J. van der Molen and L. A. M. G. van Leengoed. 1989. Difference in virulence between two strains of *Streptococcus suis* type 2 after experimentally induced infection of newborn germfree pigs. *Am. J. Vet. Res.* 50:1037-1043.

Vecht U., L. A. M. G. van Leengoed and E. R. M. Verheyen. 1985. *Streptococcus suis* infections in pigs in The Netherlands (part one). *Vet. Q.* 7:315-321.

Vecht U., H. J. Wisselink, M. L. Jellema and H. E. Smith. 1991. Identification of two proteins associated with virulence of *Streptococcus suis* type 2. *Infect. Immun.* 59:3156-3162.

Vecht U., H. J. Wisselink, J. E. van Dijk and H. E. Smith. 1992. Virulence of *Streptococcus suis* type 2 strains in newborn germfree pigs depends on phenotype. *Infect. Immun.* 60:550-556.

Vecht U., H. J. Wisselink, N. Stockhofe-Zurwieden and H. E. Smith. 1995. Characterization of virulence of the *Streptococcus suis* serotype 2 reference strain Henrichsen S735 in newborn germfree pigs. *Vet. Microbiol.* 51:125-136.

Wisselink H. J., H. E. Smith, N. Stockhofe-Zurwieden, K. Peperkamp and U. Vecht. 2000. Distribution of capsular types and production of muramidase-released protein (MRP) and extracellular factor (EF) of *Streptococcus suis* strains isolated from diseased pigs in seven European Countries. *Vet. Microbiol.* 74:237-247.

TABLE 1

Bacterial strains and plasmids

| strain/plasmid | relevant characteristics* | source/reference |
|---|---|---|
| Strain *E. coli* | | |
| XL2 blue | | Stratagene |
| *S. suis* | | |
| 10 | pathogenic serotype 2 strain | Vecht et al. |
| S735 | weak-pathogenic serotype 2 reference strain | Vecht et al. |
| 24 | weak-pathogenic serotype 2 strain | Vecht et al. |
| Plasmid | | |
| pKUN19 | replication functions pUC, $Amp^R$ | Konings et al. |
| pE194 | $Em^R$ | Horinouchi et al. |
| pMR11 | pKUN19 containing *S. suis* mrp gene | Smith et al. |
| pCOM1 | replication functions pWVO1, $Em^R$ | this work |
| pCOM-L | pCOM1 containing random sequences of *S. suis* strain 10 | this work |
| pCOM-V10 | pCOM1 containing *S. suis* strain 10 fragment selected in pigs | this work |
| pCOM-V735 | pCOM1 containing a 3.1 kb PstI-HindIII fragment from *S. suis* strain S735 (homologous to V10) | this work |

*$Spc^R$: spectinomycin resistant
$Amp^R$: ampicillin resistant
$Em^R$: erythromycin resistant

TABLE 2

Virulence of *S. suis* library and strains in germfree pigs

| strains | No. of pigs | dose | mortality[a] (%) | mean no. of days till death | morbidity[b] (%) | specific[c] symptoms | non-specific[d] symptoms | fever index[e] | leukocyte index[f] | CNS | serosa | joints |
|---|---|---|---|---|---|---|---|---|---|---|---|---|
| A | | | | | | | | | | | | |
| S735 (pCOM-L) | 4 | $10^7$ | 100 | 4 | 100 | 69 | 91 | 25 | n.a. | 3 | 2 | 3 |
| S735 (pCOM-L) | 4 | $10^8$ | 75 | 7 | 100 | 50 | 69 | 20 | 17 | 2 | 1 | 2 |
| B | | | | | | | | | | | | |
| S735 (pCOM-V10) | 5 | $10^6$ | 100 | 1 | 100 | 100 | 100 | 54 | 4 | 5 | 5 | 5 |
| S735 (pCOM1) | 4 | $10^6$ | 25 | 12 | 25 | 2 | 11 | 6 | 80 | 1 | 1 | 2 |
| C | | | | | | | | | | | | |
| S735 (pCOM-V10) | 5 | $10^6$ | 100 | 1 | 100 | 100 | 100 | 60 | n.a. | 5 | 5 | 5 |
| S735 (pCOM-V735) | 5 | $10^6$ | 20 | 15 | 100 | 40 | 26 | 17 | 52 | 1 | 1 | 1 |
| S735 (pCOM1) | 5 | $10^6$ | 20 | 16 | 60 | 11 | 9 | 11 | 20 | 1 | 0 | 0 |
| D | | | | | | | | | | | | |
| 24 (pCOM-V10) | 5 | $10^6$ | 100 | 2 | 100 | 50 | 66 | 42 | 29 | 3 | 3 | 5 |
| 24 (pCOM-V735) | 4 | $10^6$ | 25 | 15 | 100 | 40 | 30 | 17 | 18 | 1 | 0 | 0 |
| 24 (pCOM1) | 5 | $10^6$ | 20 | 15 | 20 | 2 | 14 | 6 | 21 | 1 | 0 | 0 |
| E | | | | | | | | | | | | |
| S735 (pCOM-V10) | 4 | $10^6$ | 100 | 1 | 100 | 100 | 100 | 57 | n.d. | 4 | 4 | 4 |
| S735 (pCOM-V10-ORF2) | 4 | $10^6$ | 100 | 1 | 100 | 100 | 84 | 50 | n.d. | 4 | 4 | 4 |
| S735 (pCOM-V10-ORF3) | 4 | $10^6$ | 0 | 11 | 0 | 6 | 4 | 3 | n.d. | 0 | 0 | 0 |
| S735 (pCOM1) | 4 | $10^6$ | 0 | 11 | 0 | 0 | 9 | 5 | n.d. | 0 | 0 | 0 |

[a] Percentage of pigs that died due to infection or had to be killed for animal welfare reasons
[b] Percentage of pigs with specific symptoms
[c] Percentage of observations for the experimental group in which specific symptoms (ataxia, lameness of at least one joint and/or stillness) were observed
[d] Percentage of observations for the experimental group in which non-specific symptoms (inappetite and/or depression) were observed
[e] Percentage of observations for the experimental group of a body temperature of >40° C.
[f] Percentage of blood samples for the experimental group in which the concentration of granulocytes was $>10^{10}$/liter
n.a.: not applicable
n.d.: not determined

What is claimed is:

1. An isolated, synthetic, or recombinant peptide as encoded by the nucleic acid sequence of SEQ ID NO: 14 or SEQ ID NO:15.

2. A pharmaceutical composition comprising the peptide of claim 1.

3. A diagnostic test kit comprising the peptide of claim 1.

4. An isolated, synthetic or recombinant peptide comprising an amino acid sequence selected from the group consisting of the amino acid sequence of SEQ ID NO: 10, SEQ ID NO: 11, SEQ ID NO:12 and SEQ ID NO:13.

5. A pharmaceutical composition comprising the peptide of claim 4.

6. A diagnostic test kit comprising the peptide of claim 4.

7. An isolated, synthetic or recombinant peptide encoded by a nucleic acid molecule, wherein the sequence of said nucleic acid molecule is complementary to a sequence that hybridizes to the full length sequence of SEQ ID NO: 14 and/or to the full length sequence of SEQ ID NO: 15 at 65° C. and after washing twice with a solution of 40 mM sodium phosphate (pH 7.2), 1 mM EDTA and 5% sodium dodecyl sulphate for 30 minutes at 65° C. and washing twice with a solution of 40 mM sodium phosphate (pH 7.2), 1 mM EDTA and 1% sodium dodecyl sulphate for 30 min at 65° C.

8. The peptide of claim 7, wherein the nucleic acid molecule encodes for a peptide having the amino acid sequence of SEQ ID NO: 10, SEQ ID NO: 11, SEQ ID NO: 12, or SEQ ID NO: 13.

9. A pharmaceutical composition comprising the peptide of claim 7.

10. A diagnostic test kit comprising the peptide of claim 7.

11. A peptide comprising the amino acid sequence encoded by the nucleic acid sequence comprising SEQ ID NO: 14 or SEQ ID NO:15, wherein the peptide is an isolated, synthetic, or recombinant peptide.

12. A pharmaceutical composition comprising the peptide of claim 11.

13. A diagnostic test kit comprising the peptide of claim 11.

14. A peptide comprising the amino acid sequence of SEQ ID NO: 10, SEQ ID NO: 11, SEQ ID NO: 12, or SEQ ID NO: 13, wherein the peptide is an isolated, synthetic, or recombinant peptide.

15. A pharmaceutical composition comprising the peptide of claim 14.

16. A diagnostic test kit comprising the peptide of claim 14.

* * * * *

UNITED STATES PATENT AND TRADEMARK OFFICE
CERTIFICATE OF CORRECTION

PATENT NO. : 8,071,111 B2
APPLICATION NO. : 12/592923
DATED : December 6, 2011
INVENTOR(S) : Hilda Elizabeth Smith Page 1 of 1

It is certified that error appears in the above-identified patent and that said Letters Patent is hereby corrected as shown below:

In the Specification:
    COLUMN 1,   LINE 15,   Change "Jan. 15, 2004," to --Nov. 9, 2000,--

Signed and Sealed this
Fourth Day of June, 2013

Teresa Stanek Rea
*Acting Director of the United States Patent and Trademark Office*